United States Patent
Meyer et al.

(10) Patent No.: US 7,583,998 B2
(45) Date of Patent: Sep. 1, 2009

(54) MULTI-CHAMBER CARDIAC CAPTURE DETECTION USING CROSS CHAMBER SENSING

(75) Inventors: Scott A. Meyer, Rochester, MN (US); David J. Yonce, Fridley, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 587 days.

(21) Appl. No.: 11/157,426

(22) Filed: Jun. 21, 2005

(65) Prior Publication Data
US 2006/0287685 A1    Dec. 21, 2006

(51) Int. Cl.
*A61N 1/37* (2006.01)
(52) U.S. Cl. .......................................... 607/28; 607/27
(58) Field of Classification Search ................ 600/510; 607/28, 27
See application file for complete search history.

(56) References Cited

U.S. PATENT DOCUMENTS

| | | | |
|---|---|---|---|
| 6,128,535 A | 10/2000 | Maarse | |
| 6,148,234 A | 11/2000 | Struble | |
| 6,169,921 B1 | 1/2001 | KenKnight et al. | |
| 6,226,551 B1 | 5/2001 | Zhu et al. | |
| 6,363,281 B1 * | 3/2002 | Zhu et al. | 607/28 |
| 6,456,881 B1 | 9/2002 | Bornzin et al. | |
| 6,697,673 B1 | 2/2004 | Lu | |
| 6,768,924 B2 | 7/2004 | Ding et al. | |
| 7,228,172 B2 | 6/2007 | Jarverud et al. | |
| 2001/0049543 A1 | 12/2001 | Kroll | |
| 2002/0087200 A1 | 7/2002 | Zhu et al. | |
| 2003/0083710 A1 | 5/2003 | Ternes et al. | |
| 2003/0083711 A1 | 5/2003 | Yonce et al. | |
| 2003/0195579 A1 * | 10/2003 | Bradley et al. | 607/27 |

* cited by examiner

*Primary Examiner*—Carl H. Layno
*Assistant Examiner*—Tammie K Heller
(74) *Attorney, Agent, or Firm*—Hollingsworth & Funk, LLC

(57) ABSTRACT

Methods and systems involve multi-chamber cardiac capture detection utilizing sensing during a cross-chamber refractory period. First and second pacing pulses are delivered to first and second heart chamber. Capture or non-capture of the second heart chamber is determined. Sensing in the first heart chamber is performed to sense for cross-chamber propagation initiated by the second pacing pulse. Capture of the first chamber is detected if capture of the second heart chamber is detected and if the cross-chamber propagation is not detected.

13 Claims, 25 Drawing Sheets

MULTI-CHAMBER CARDIAC CAPTURE DETECTION USING CROSS CHAMBER SENSING

FIELD OF THE INVENTION

The present invention relates generally to implantable medical devices and, more particularly, to determining capture of one or more heart chambers.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. A pacing pulse that causes a sufficient depolarization of the myocardium, producing a propagating wave of excitation produces a contraction. A pacing pulse that does not produce capture wastes energy from the limited energy resources (battery) of pacemaker, and can have deleterious physiological effects as well. A pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration or width. Programmable pacemakers enable the amplitude and pulse width of pacing pulses to be adjusted, along with other parameters. It is therefore desirable to perform a capture verification test at selected times in order to ascertain whether capture is being achieved by a pacemaker so that such parameters can be adjusted if needed.

It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

SUMMARY OF THE INVENTION

The present invention involves various methods and devices for detecting capture of one or more heart chambers.

One embodiment of the invention involves a capture detection method. The method includes delivering a first pacing pulse to a first heart chamber and a second pacing pulse to a second heart chamber. Capture or non-capture of the second heart chamber is determined. Sensing in the first heart chamber is performed to sense for a propagating cardiac response initiated by the second pacing pulse. Capture of the first chamber is detected if capture of the second heart chamber is detected and if the propagating cardiac response is not detected.

Another embodiment of the invention is directed to a cardiac rhythm management system. The system includes cardiac electrodes configured to electrically couple to a heart. A pulse generator is coupled to the cardiac electrodes and is configured to deliver pacing pulses to first and second heart chambers. A sensing circuit is configured to sense cardiac electrical signals including a propagating cardiac response initiated by the second pacing pulse. A capture detection circuit is coupled to the sensing circuit and the cardiac electrodes. The capture detection circuit is configured to determine if the second pacing pulse captured the second heart chamber and to detect capture of the first heart chamber if capture of the second heart chamber is detected and if the propagating cardiac response is not detected.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
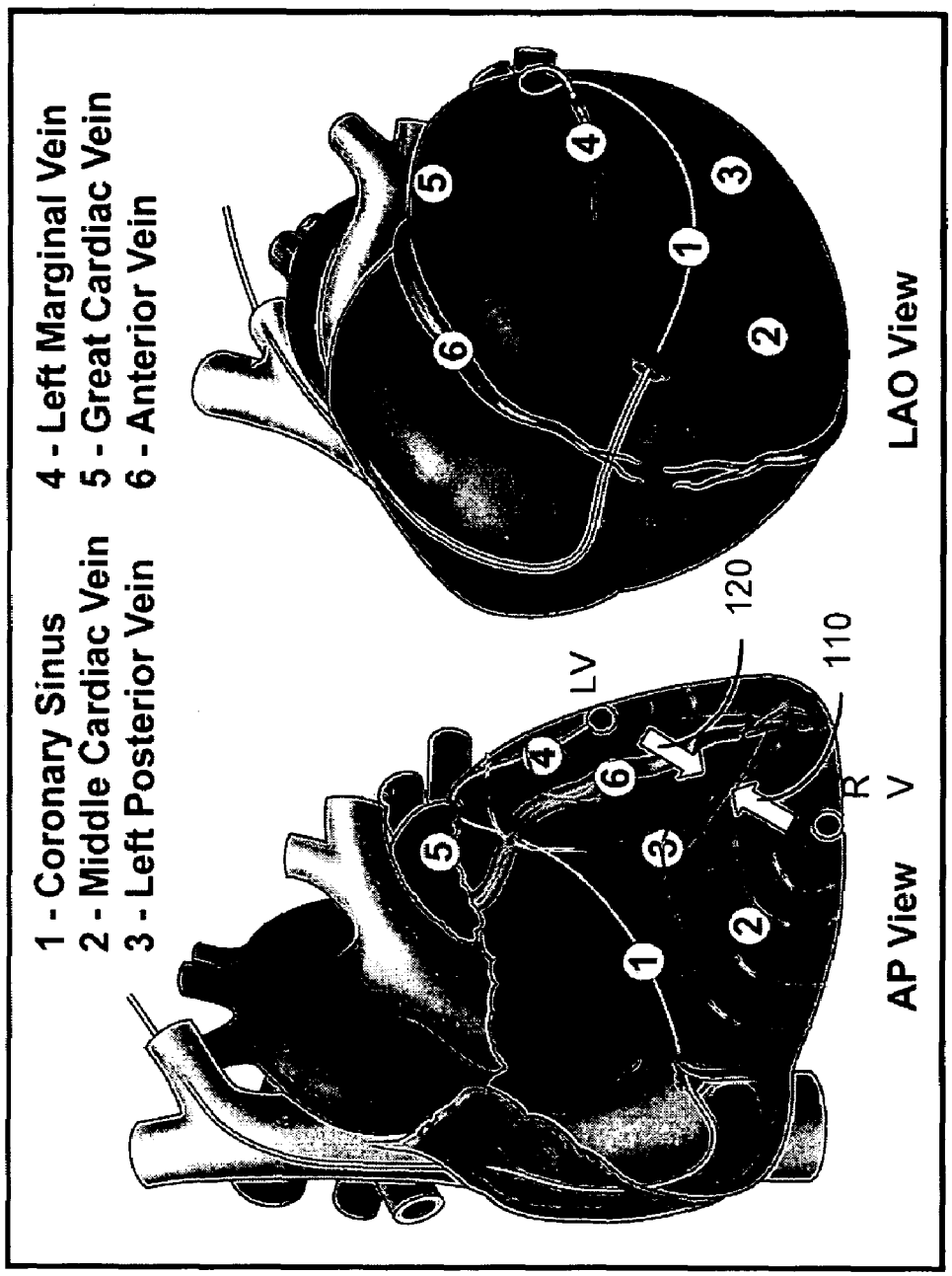
FIG. 1 is a diagram illustrating a propagating wavefront of electrical activation produced by capture of the right ventricle moving toward the left ventricle.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Pacemakers, which may include, for example, pacemaker/defibrillators, and/or cardiac resynchronizers, are used to regulate heart rhythm. These devices typically include a pulse generator that generates pacing pulses delivered to one or more heart chambers through implanted electrodes. The pacing pulses stimulate tissue adjacent the electrodes. If a pacing pulse has sufficient energy to "capture" the heart tissue, then the heart chamber contracts producing a paced cardiac beat.

A pacemaker may be used, for example, to regulate a heart rhythm that is too slow or is insufficiently coordinated to produce hemodynamically effective pumping action. Pacemakers typically have a programmable electronic controller that causes the pacing pulses to be output in response to lapsed time intervals and sensed electrical activity (i.e., intrinsic heart beats). Most pacemakers are programmed to operate in a so-called demand mode where a pacing pulse is delivered to a heart chamber during a cardiac cycle only when no intrinsic beat by the chamber is detected. An escape interval is defined for the paced chamber, which is the minimum time interval in which an intrinsic beat must be detected before a pace will be delivered. The ventricular escape interval thus defines the minimum rate at which the pacemaker will allow the heart to beat, sometimes referred to as the lower rate limit. If functioning properly, the pacemaker makes up for a heart's inability to pace itself at an appropriate rhythm.

Also included within the concept of cardiac rhythm is the manner and degree to which the heart chambers contract in a coordinated manner during a cardiac cycle to produce efficient pumping of blood. The heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses in a manner that results in a coordinated contraction of both atria and both ventricles. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output. The resulting reduction in cardiac output may be significant in a patient with congestive heart failure (CHF) whose cardiac output is already compromised. Intraventricular and/or interventricular conduction defects can also be a cause of CHF in some patients. In order to treat these problems, pacemakers have been developed which provide multi-site electrical pacing stimulation to one or both atria and/or one or both ventricles during a cardiac cycle in an attempt to improve the coordination of atrial and/or ventricular contractions. Therapy that is delivered to improve the coordination of atrial and/or ventricular contractions is sometimes denoted cardiac resynchronization therapy. To optimize the cardiac output for some heart failure patients, for example, the right and left ventricles may be paced in sequence with a determined time offset between the right and left ventricular paces. This type of therapy is termed biventricular pacing.

Multi-chamber capture determination methodologies in accordance with embodiments of the invention are based on cancellation of depolarization wavefronts caused by paced or sensed cardiac events occurring in bilateral cardiac chambers, e.g., right and left ventricles. In one exemplary situation, after sequentially pacing both ventricles, the system senses for cardiac activity in the first-paced ventricle during a cross-chamber sensing window that follows the pacing pulse delivered to the second-paced ventricle. If both pacing pulses captured their respective chambers, the depolarization wavefront of the first-paced ventricle collides with a depolarization wavefront of the second-paced ventricle and cancels the cardiac activity in the first-paced ventricle during the cross chamber sensing window. If the first-paced ventricle was not captured, then no cancellation occurs, and cardiac activity responsive to the activation of the second paced chamber is evident in the cross chamber sensing window.

The processes involved in capture detection methodologies in accordance with embodiments of the invention are illustrated in the diagrams of FIGS. 1-4. FIGS. 1-4 pertain to biventricular pacing, however, the concepts are similarly applicable to biatrial pacing. As illustrated in FIG. 1, capture of the right ventricle produces a propagating wavefront of electrical activation 110 moving toward the left ventricle. Capture of the left ventricle produces a propagating wavefront of electrical activation 120 moving toward the right ventricle. The wavefronts 110,120 from the right and left ventricles collide and interact at a point between the pacing electrodes. At the point of collision, each wavefront 110, 120 meets refractory tissue and the wavefronts 110, 120 annihilate one another.

Figure 2:
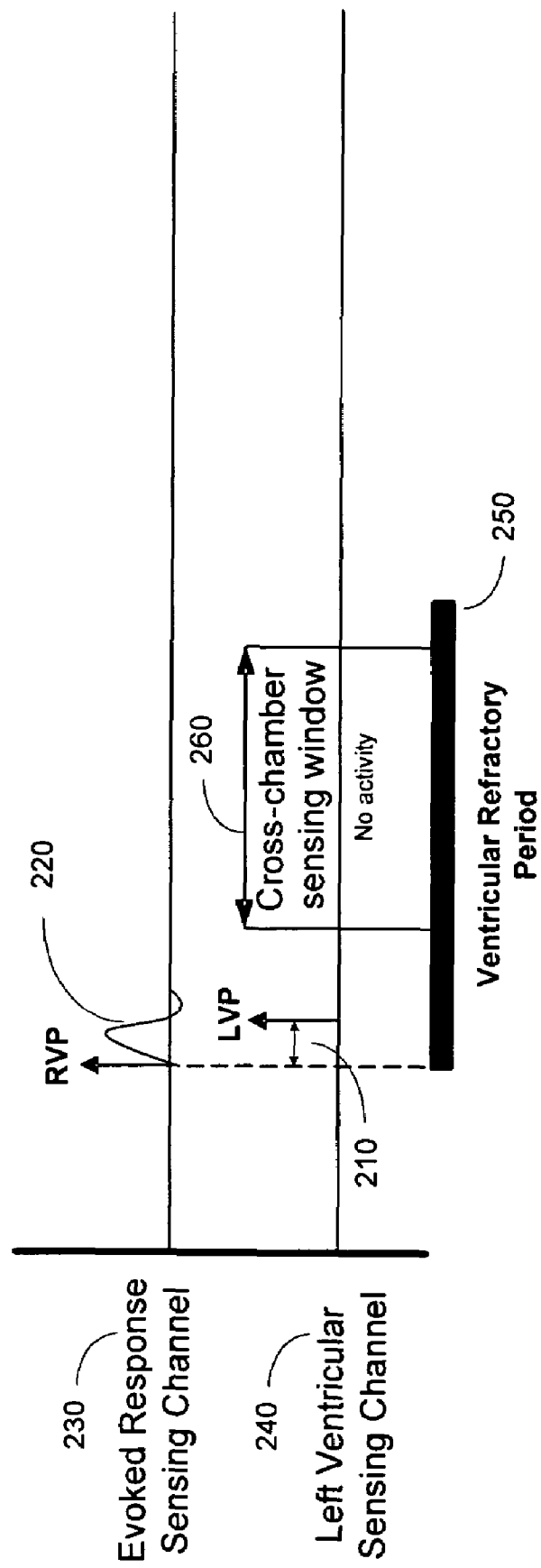
FIG. 2 illustrates a timing diagram of paced events and sensed signals in the right and left ventricles illustrating capture of both ventricles.

FIG. 2 illustrates a timing diagram of paced events and sensed signals in the right and left ventricles illustrating capture of both ventricles. In this scenario, a right ventricular pacing pulse (RVP) is delivered to the right ventricle. A left ventricular pacing pulse (LVP) is delivered to the left ventricle slightly delayed from the time of delivery of the RVP. Delivery of the RVP and LVP may be separated in time by an interventricular delay 210, such as an interventricular delay 210 of up to about 100 ms. In various embodiments, either the left ventricle or the right ventricle may be paced first.

The right ventricular cardiac signal following the RVP may be sensed by a right ventricular sensing channel or by a dedicated evoked response (ER) sensing channel 230, for example. If the RVP captures the right ventricle, then a right ventricular evoked response 220 is present on the ER sensing channel 230. The left ventricular cardiac signal may be sensed following the LVP, for example, using a left ventricular sensing channel 240. If the left ventricle is captured by the LVP, the left ventricular cardiac tissue becomes refractory for a period of time 250 following activation of the left ventricular tissue. The refractoriness of the left ventricular cardiac tissue after capture prevents a signal produced by the right ventricular depolarization wavefront 110 (FIG. 1) from appearing on the left ventricular sensing channel 240 during a cross-chamber sensing window 260. The lack of cardiac signal sensed on the left ventricular sensing channel 240 during the cross-chamber sensing window 260 following delivery of the LVP in addition to the evoked response of the right ventricle produced by the RVP indicates capture of the right and the left ventricles. Detecting capture of the right ventricle or an intrinsic right ventricular event confirms bradycardia pacing support. Detecting capture of the right ventricle or an intrinsic right ventricular event in addition to capture of the left ventricle confirms biventricular pacing support. Detecting a lack of cardiac signal sensed on the left ventricular sensing channel 240 alone may not confirm bradycardia or biventricular pacing support. For example, if both ventricles were not captured, then there would be no signal on the left ventricular sensing channel 240.

Figure 3:
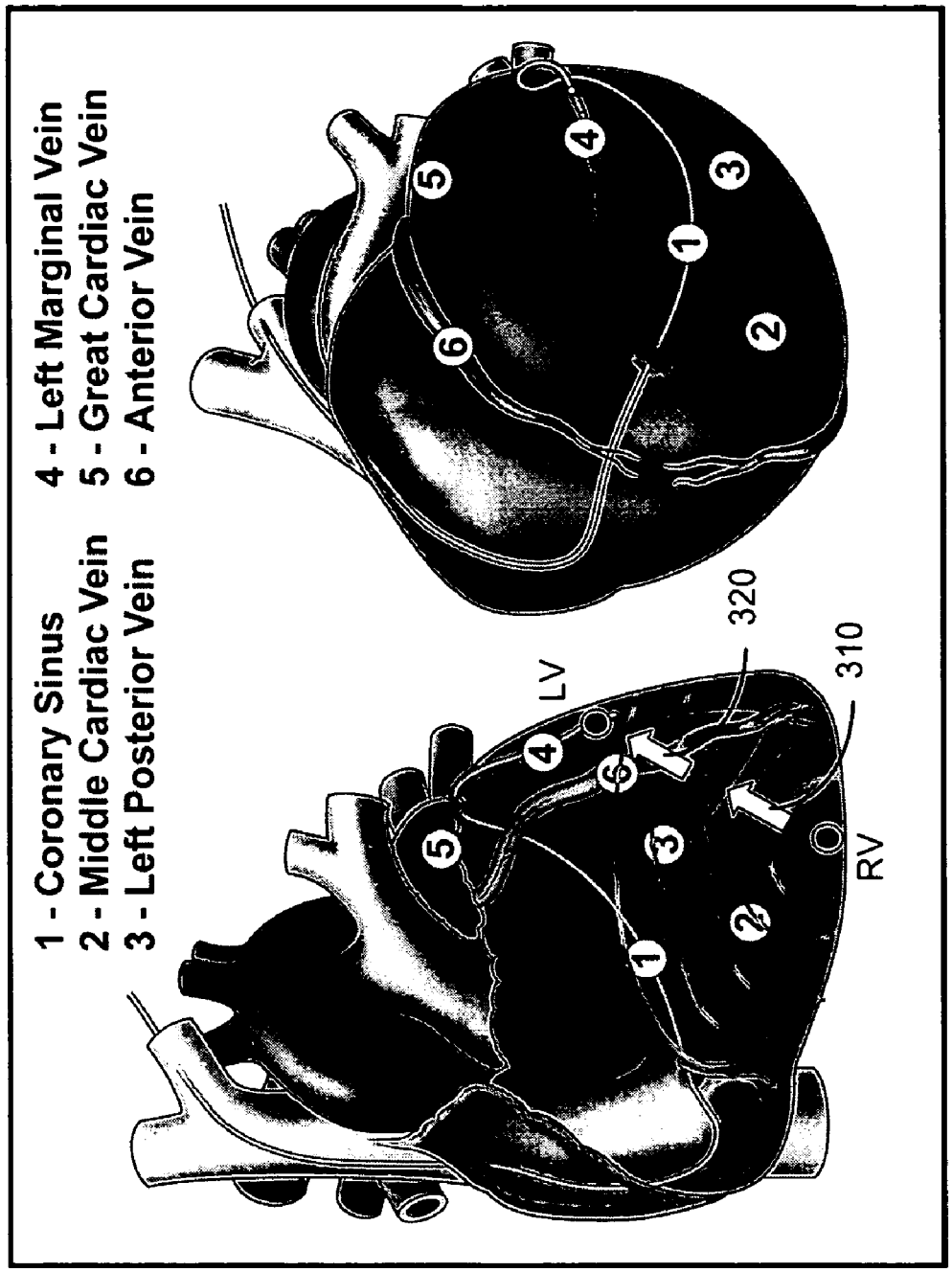
FIG. 3 is a diagram illustrating capture of the right ventricle with non-capture of the left ventricle during a cardiac cycle.

FIG. 3 illustrates capture of the right ventricle with non-capture of the left ventricle during a cardiac cycle. Capture of the right ventricle initiates a propagating wavefront of electrical activation that starts 310 in the right ventricle and travels toward the left ventricle. If the left ventricle is not captured by the pacing pulse delivered to the left ventricle, there is no opposing depolarization wavefront traveling from the left to the right ventricles. The left ventricular tissue does not become refractory and the depolarization wavefront initiated by right ventricular capture continues 320 to the left ventricle.

Figure 4:
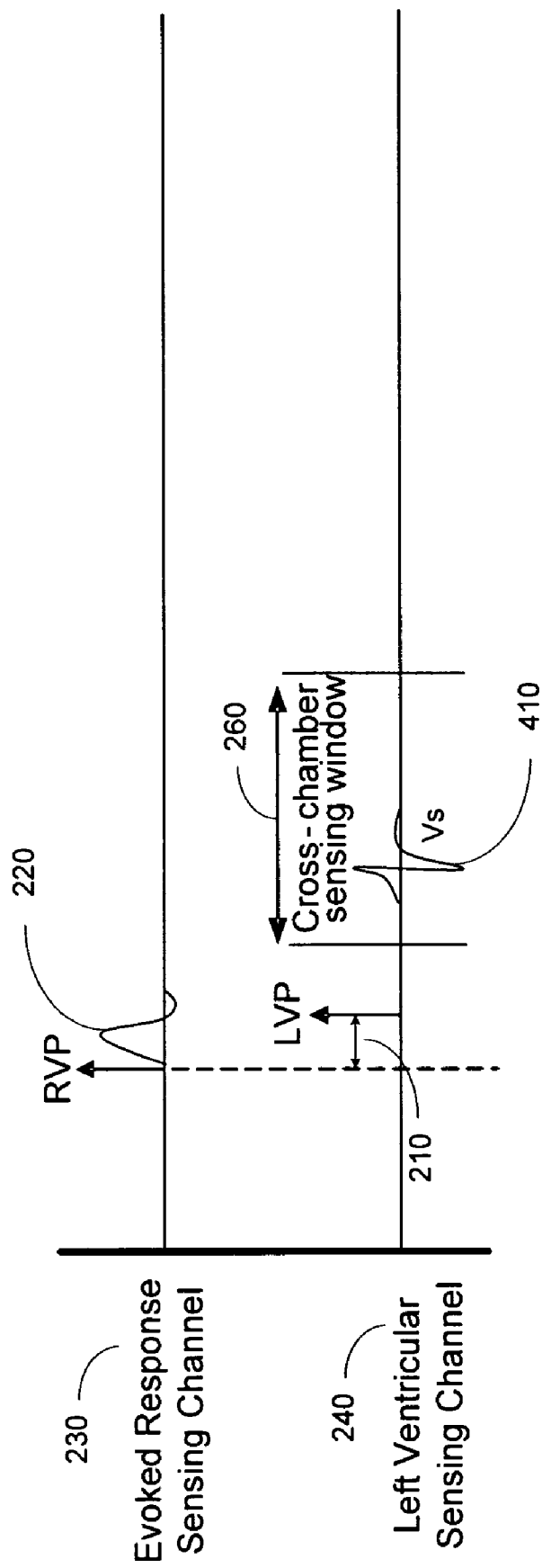
FIG. 4 is a timing diagram illustrating paced events and sensed signals for biventricular pacing resulting in right ventricular capture and left ventricular non-capture in accordance with embodiments of the invention.

The timing diagram of FIG. 4 illustrates paced events and sensed signals for biventricular pacing resulting in right ventricular capture and left ventricular non-capture. In this scenario, a right ventricular pacing pulse (RVP) is delivered to the right ventricle. A left ventricular pacing pulse (LVP) is delivered to the left ventricle slightly delayed from the time of delivery of the RVP. Delivery of the RVP and LVP may be separated in time by an interventricular delay 210, such as an interventricular delay 210 of up to about 100 ms. In various embodiments, either the left ventricle or the right ventricle may be paced first.

In this example, the right ventricular cardiac signal following the RVP is sensed by a dedicated evoked response (ER) sensing channel 230. The RVP captures the right ventricle and a right ventricular evoked response 220 is present on the ER sensing channel 230. The left ventricular cardiac signal is sensed following the LVP using a left ventricular sensing channel 240. In this example, the left ventricle is not captured by the LVP and initiation of a propagating wavefront of cardiac activation from the left ventricle does not occur. The left ventricular cardiac tissue does not become refractory. The non-refractoriness of the left ventricular cardiac tissue allows the right ventricular depolarization wavefront 320 (FIG. 3) to propagate to the left ventricle. A signal Vs 410 sensed on the left ventricular sensing channel 240 during a cross-chamber sensing window 260 indicates capture of the right ventricle and non-capture of the left ventricle.

Figure 5A:
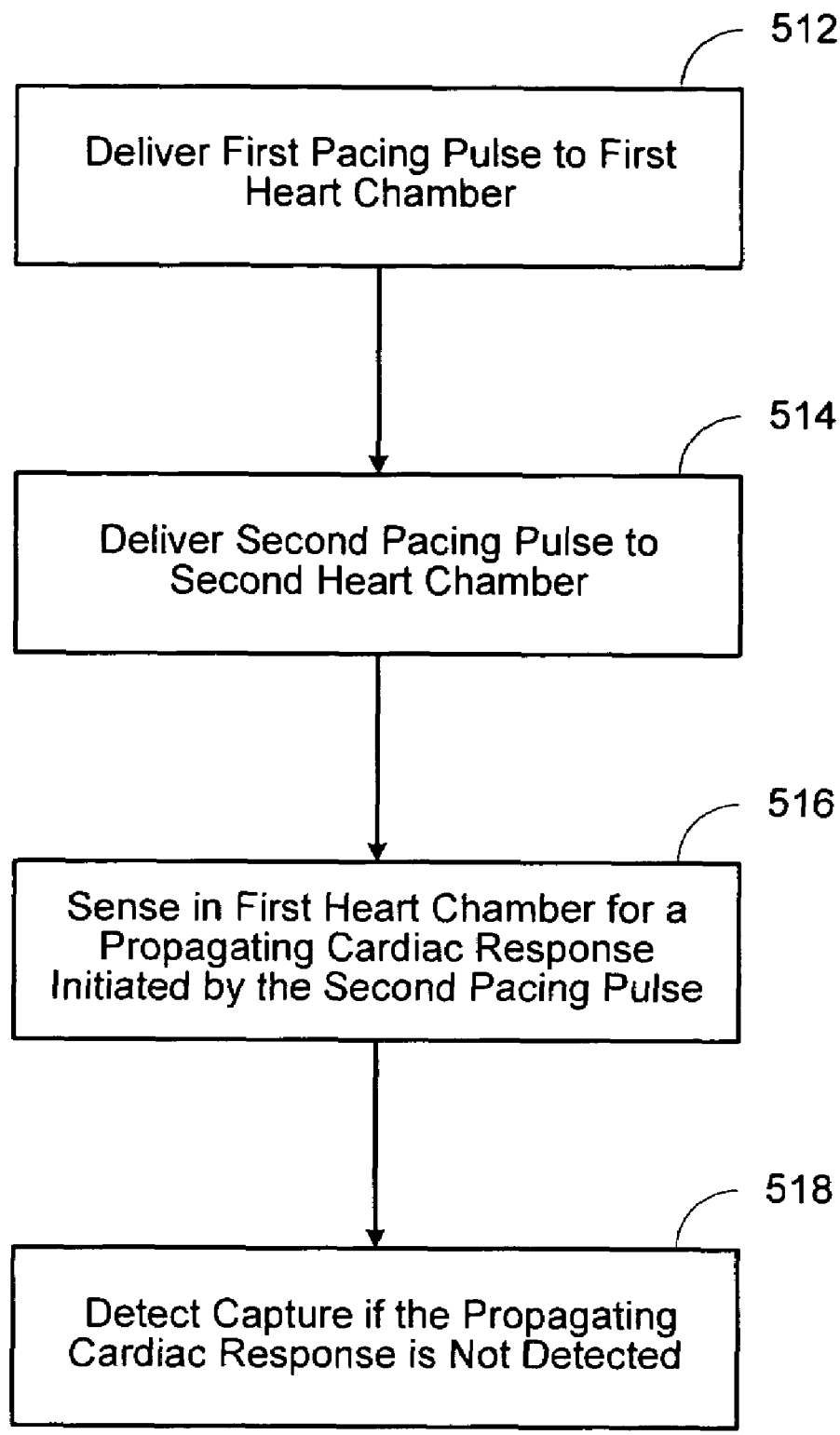
FIG. 5A is a flowchart illustrating a capture detection method for multi-chamber pacing in accordance with embodiments of the invention.

The electrophysiological events described above may be used to determine capture of one or both chambers during biatrial and/or biventricular pacing. The flowchart of FIG. 5A illustrates a capture detection method for multichamber pacing in accordance with embodiments of the invention. In this implementation, both chambers are paced. First and second pacing pulses are delivered to first and second heart chambers, respectively 512, 514. The first and second heart chambers may comprise bilateral heart chambers, e.g., first and second ventricles or first and second atria. The pacing pulses may be delivered substantially simultaneously. Alternatively, the first and the second pacing pulses may be separated by an interventricular delay. In one scenario, the right ventricle or atrium is paced before the left ventricle or atrium. In another scenario the left ventricle or atrium is paced before the right ventricle or atrium.

The system senses 516 in the first heart chamber for a propagating cardiac response initiated by the second pacing pulse. If the propagating cardiac response is not sensed 518 in the first heart chamber, then capture of the first heart chamber is detected. If the propagating cardiac response is sensed, then non-capture of the first heart chamber is detected.

Figure 5B:
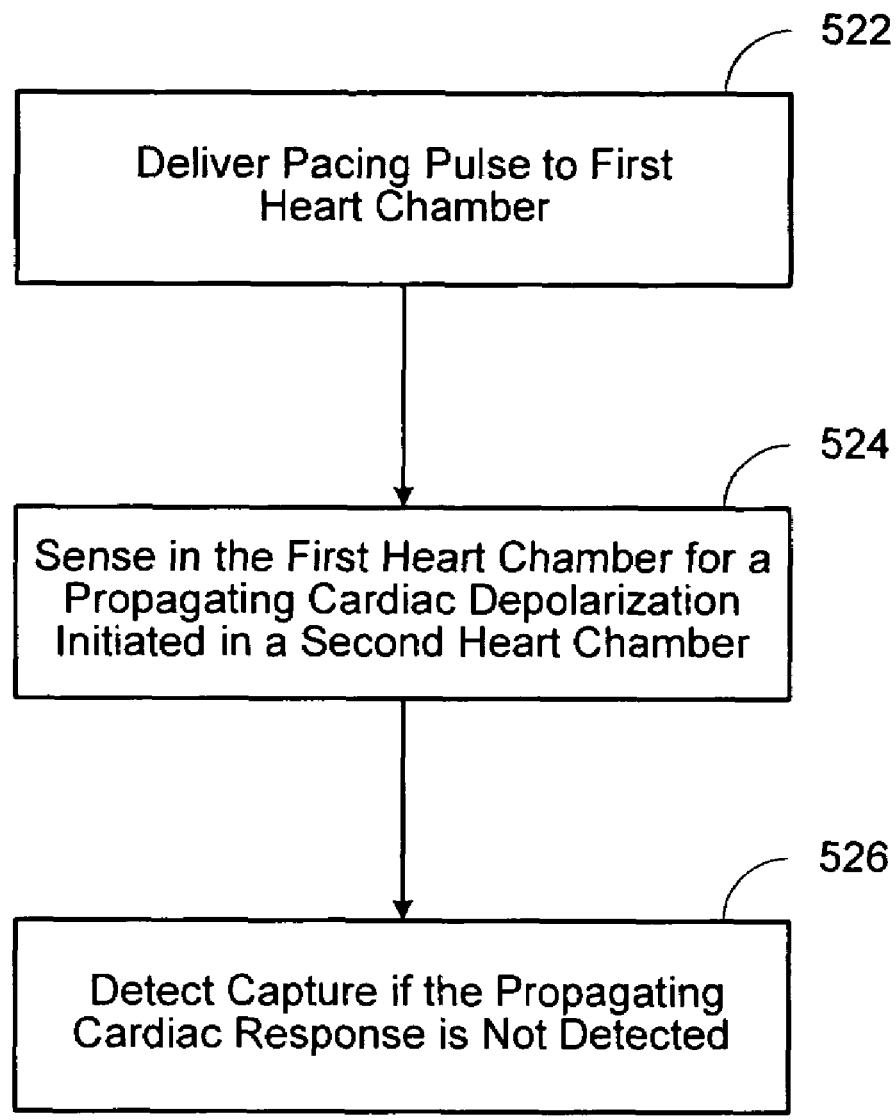
FIG. 5B is a flowchart illustrating capture detection wherein a first heart chamber is paced and a second heart chamber is paced or intrinsically depolarizes in accordance with embodiments of the invention.

FIG. 5B is a flowchart illustrating capture detection wherein a first heart chamber is paced and a second heart chamber is paced or intrinsically depolarizes. A pacing pulse is delivered 522 to a first heart chamber. The system senses in the first chamber for a propagating cardiac depolarization initiated in the second heart chamber. If the propagating cardiac depolarization is not sensed 524, then capture is detected 526. The depolarization may be caused by an intrinsic depolarization, or capture of the second heart chamber. In some embodiments, the system may sense only in one the first chamber. In other embodiments, system may also sense in the second chamber for an intrinsic or capture response. Capture of the second heart chamber may be detected using, for example, any of the methods described in connection with FIG. 3 above.

Multi-chamber pacemakers are used to provide both bradycardia therapy and cardiac resynchronization therapy. Bradycardia therapy maintains a heart rate above a lower rate limit. Cardiac resynchronization therapy involves pacing bilateral heart chambers, e.g., right and left ventricles, substantially simultaneously, or in phased sequence to promote an effective pumping action of the heart. Various embodiments of the invention are directed to confirming that one or both of bradycardia therapy and cardiac resynchronization therapy are delivered to the heart. FIG. 6 is a flowchart depicting a process that may be used to confirm bradycardia therapy and/or resynchronization therapy for left and right ventricles.

Cardiac resynchronization therapy may involve pacing one or both ventricles following an atrioventricular delay (AVD). The atrioventricular delay interval may be initiated by an intrinsic depolarization of an atrium or a pacing pulse delivered to an atrium. The biventricular therapy may be delivered relative to the AVD.

Biventricular therapy may involve pacing or sensing the left ventricle and pacing or sensing the right ventricle. In some implementations, pacing pulses are delivered to both the left and the right ventricles substantially simultaneously, e.g., within 5 msec. In some implementations, the pacing pulses delivered to the left and the right ventricles are separated by an interventricular delay (IVD) interval. For example, a biventricular therapy may involve pacing the one ventricle after expiration of the atrioventricular delay, initiating an interventricular delay relative to the delivery of the left ventricular pace, and pacing the other ventricle after expiration of the interventricular delay.

In some cases, biventricular therapy may involve pacing one ventricle prior to the expiration of an AVD interval. For example, biventricular therapy may involve delivering a first pacing pulse upon or after expiration of an atrioventricular delay and delivering a second pacing pulse relative to the delivery of the first pacing pulse. Delivering the second pacing pulse relative to the delivery of the first pacing pulse may involve delivering the second pacing pulse before or after the first pacing pulse. If the second pacing pulse is delivered before the first pacing pulse, then the second pacing pulse is delivered prior to the expiration of the atrioventricular delay.

Biventricular therapy may involve triggering delivery of a pace to one ventricle after an intrinsic depolarization of the other ventricle is sensed. For example, biventricular therapy may involve sensing an intrinsic depolarization of the right ventricle, initiating an interventricular delay interval, and pacing the left ventricle after expiration of the interventricular delay. Alternatively, biventricular therapy may involve sensing an intrinsic depolarization of the left ventricle, initiating an interventricular delay interval, and pacing the right ventricle after expiration of the interventricular delay. Biventricular therapy may involve inhibiting the delivery of a scheduled ventricular pace to a ventricle based on sensing an intrinsic depolarization of the ventricle.

By way of example, the processes of the present invention may be used to enhance capture threshold testing to determine the optimal energy for pacing. Determination of the optimal pacing energy may be implemented, for example, by an automatic capture threshold testing procedure executed by an implantable cardiac rhythm management system. Additionally, automatic capture verification may be used to monitor pacing on a beat-by-beat basis. Automatic capture verification may be used to control back up pacing when a pace pulse delivered to the heart fails to evoke a captured response (CR). These and other applications may be enhanced by employment of the systems and methods of the present invention.

Those skilled in the art will appreciate that reference to a capture threshold procedure indicates a method of determining the capture threshold in one of the left atrium, the right atrium, the left ventricle, and the right ventricle. In such a procedure, the pacemaker, automatically or upon command, initiates a search for the capture threshold of the selected heart chamber or chambers. The capture threshold is defined as the lowest pacing energy that consistently produces a contraction of the heart chamber.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. After the predetermined number of loss-of-capture events occur, the pacemaker may increase the stimulation energy in discrete steps until a predetermined number of capture events occur to confirm the capture threshold. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern.

Automatic capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 90-110 ms after the initial pace pulse. If a predetermined number of pace pulses delivered during normal pacing do not produce a captured response, the pacemaker may initiate a capture threshold test to determine the capture threshold. Automatic capture detection and back up pacing may be implemented using the cardiac response classification processes of the present invention.

Programmable pacemakers enable the amplitude and pulse width of pacing pulses to be adjusted, along with other parameters. The capture threshold may be determined by using a capture threshold test that initially paces with a high energy to ensure capture and then progressively lowers the pacing pulse energy during a sequence of cardiac cycles until capture is no longer achieved. The capture threshold may alternatively be determined by ramping up the pacing energy, or by using another search algorithm. The capture threshold determination process may be implemented in a clinical setting under the supervision of a physician, may be implemented automatically by the pacemaker, or may be initiated through an advanced patient management interface. Once the capture threshold is known for each chamber, the pacing pulse energies for the respective chambers can then be adjusted to an appropriate value for consistent capture for the chambers.

During delivery of pacing therapy to the patient, the pacemaker may detect loss of capture. Loss of capture refers to the situation wherein the energy of the pacing pulses is no longer sufficient to capture the heart tissue and produce a contraction. Loss of capture may be determined, for example, if noncapture of the chamber is detected for a predetermined number of beats, e.g., about 3 of about 5 beats. If loss of capture occurs, a capture threshold test may be scheduled.

After pacing a heart chamber, the pacemaker may determine that a delivered pacing pulse did not capture the heart chamber. In this situation, the pacemaker may adjust the pacing energy delivered by the pacemaker to the chamber, deliver a back-up pace and/or schedule a capture threshold test. Determining capture or noncapture of a heart chamber beat-by-beat is typically referred to as automatic capture verification. An automatic capture verification function provides the pacemaker with extended longevity, greater ease of use, and greater patient safety.

A pacemaker may detect capture by sensing for an evoked response in a capture detection window that starts after the delivery of the pacing pulse. Pacemakers often include one or more sensing channels for sensing intrinsic activity in the heart chambers. Sensing channels are normally rendered refractory (i.e., insensitive) for a specified time period immediately following a pace in order to prevent the pacemaker from mistaking a pacing pulse or afterpotential for an intrinsic beat. This may be accomplished by the pacemaker controller ignoring sensed events during the refractory intervals. Refractory intervals may be defined for atrial and ventricular sensing channels and with respect to both atrial and ventricular paced events.

Furthermore, a separate period that overlaps the early part of a refractory interval may also be defined, denoted a blanking interval, during which the sense amplifiers are blocked from receiving input in order to prevent their saturation during and after a pacing pulse. If the same sensing channels are used for both sensing intrinsic activity and evoked responses, the interval of time that the pacemaker senses for an evoked response must therefore be defined as a period that supercedes the normal refractory period so that the sensing circuitry within the pacemaker becomes sensitive to an evoked P-wave or R-wave.

In embodiments described herein, a dedicated evoked response sensing channel, separate from the sensing channels used to sense intrinsic activity, is utilized. The evoked response channel is used to sense signals for capture detection. The separate evoked response channel may be coupled to electrodes in one or more heart chambers through a switch matrix. Such an arrangement allows various electrode pairs to be coupled to the evoked response channel for detecting capture in multiple chambers.

In some implementations, capture verification is performed by delivering a pacing pulse and sensing for an evoked response using the same electrode. However, the induced polarization that builds up on an electrode after a pacing pulse is delivered may interfere with sensing the evoked response if the same electrode is used for pacing and sensing. Furthermore, because an evoked response is a wave of depolarization that necessarily moves away from a pacing electrode responsible for the depolarization, sensing for an evoked response may be performed more effectively using an electrode other than the electrode used for pacing. Using a separate evoked response channel that may be connected through a switch matrix to various electrodes facilitates the use of a first set of electrodes for pacing and a different set of electrodes for sensing for an evoked response.

In a multiple chamber pacing regimen, capture verification based upon sensing for an evoked response of individual chambers may not be accurate. In biventricular pacing, for example, the proximity in time of resynchronization paces to the left and right ventricles may prevent an evoked response caused by the first pace from being distinguished from an electrical signal generated by the second pace. In addition, the electrical signal generated by the second pace could interfere with evoked response sensing when the evoked response from the first pace occurs within an amplifier blanking interval initiated by the second pace.

Various embodiments of the invention are directed methods and systems for determining capture of multiple heart chambers. The approaches described herein may be used, for example, to provide beat-to-beat biventricular or biatrial automatic capture verification. Further, the approaches described herein may be used in connection with automatic capture threshold testing for multichamber devices. In various embodiments, a single evoked response sensing channel may be used in connection with automatic capture threshold testing for each pacing channel, e.g., right atrial, left atrial, right ventricular and/or left ventricular pacing channels.

Automated threshold testing can be achieved by connecting appropriate electrodes to via a switch matrix to the evoked response sensing amplified and testing each channel individually. A similar approach may not be effective for implementing automatic capture verification beat-by-beat during multichamber pacing. Sensing for the evoked responses of multiple chambers during multichamber pacing may be precluded due to blanking schemes and cross-chamber interference. Cross chamber interference and blanking can swamp the evoked responses, degrading the automatic capture detection performance. This situation is exacerbated with the use of an interchamber pacing delay. For example, biventricular pacing therapy may involve pacing a first ventricle and then pacing a second ventricle after an interventricular delay, e.g., a delay of about −100 ms to about 100 ms.

In one approach the ventricular beat-to-beat automatic capture detection feature senses for either an evoked response of the right or the left ventricle depending on the interventricular delay. For example, if the pace timing offset between the right ventricle (RV) and the left ventricle (LV) is positive (RV paced prior to LV), then the system senses for an evoked response of the left ventricle for beat to beat automatic capture detection. In this case, the RV evoked response may be hidden in the LV pace. The LV evoked response occurs after both paces and may provide the cleanest evoked response. If the pace timing offset between the right ventricle (RV) and the left ventricle (LV) is negative (LV paced prior to RV) then the system senses for an evoked response of the right ventricle. If the channels are simultaneously pace, e.g., paced within 5 msec of each other, then either channel may be used.

The above described automatic capture detection process ensures that the heart contracted following biventricular pacing, confirming bradycardia therapy, but not heart failure therapy. An autothreshold algorithm, utilized, for example at preset intervals such as once per hour, may be used to confirm the delivery of heart failure therapy. In this mode, the automatic capture detection algorithm ensures patient safety by confirming bradycardia therapy on a beat to beat basis and the autothreshold test confirms heart failure therapy on a periodic basis.

Figure 6A:
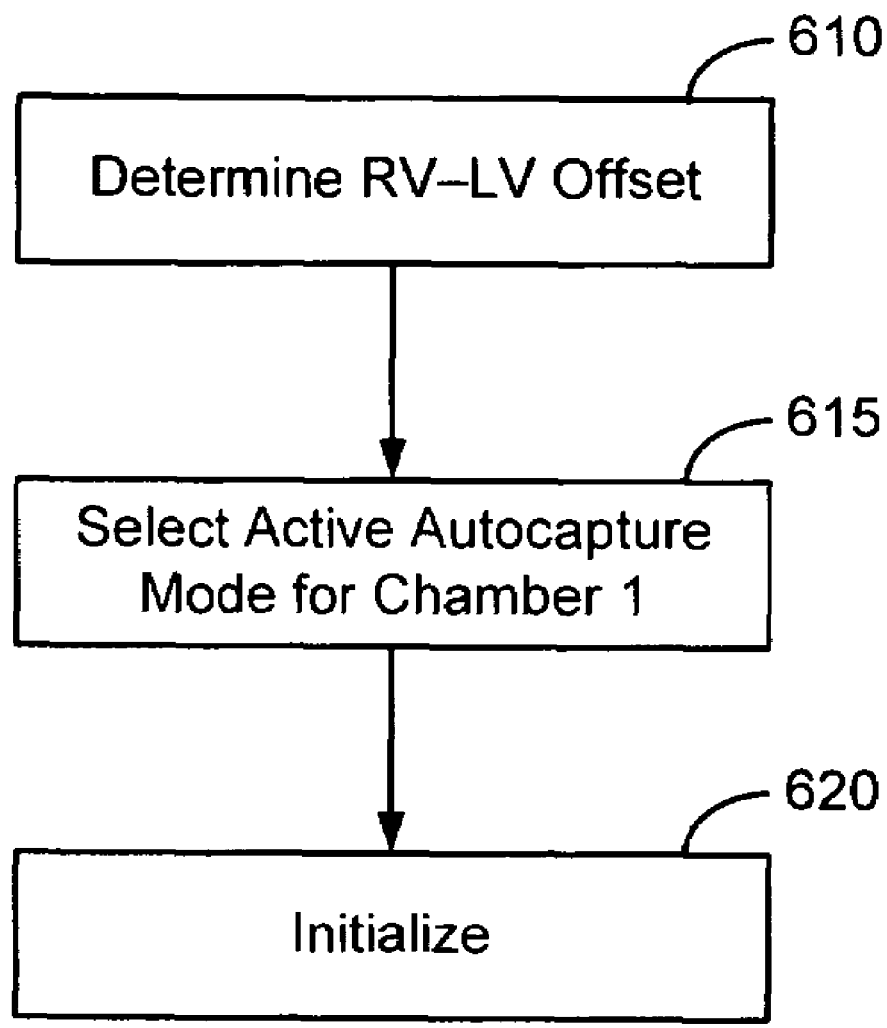
FIGS. 6A and 6B are flowcharts illustrating an automatic capture detection process for biventricular pacing in accordance with embodiments of the invention.
Figure 6B:
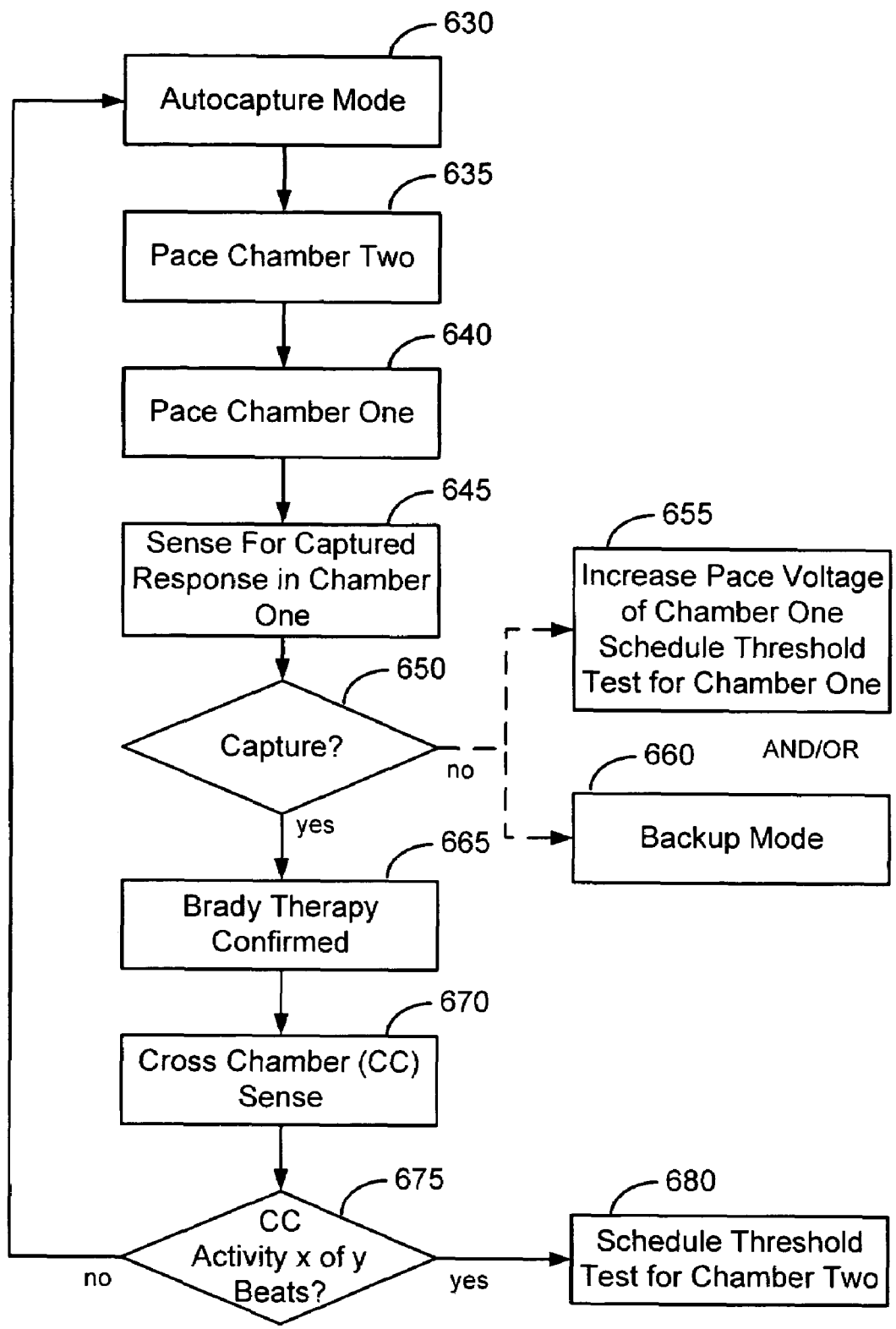

The flowcharts of FIGS. 6A and 6B illustrate an automatic capture detection process for biventricular pacing in accordance with embodiments of the invention. In FIG. 6A, the RV-LV offset is determined 610. A chamber is selected 615 for active automatic capture mode depending on the RV-LV offset. For example, if the RV-LV offset is positive, i.e., the RV is paced before the LV, the LV is selected as the active chamber, designated chamber 1, for automatic capture detection. However, if the RV-LV offset is negative, i.e., the LV is paced before the RV, then the RV is selected as the active chamber for automatic capture detection. If the RV and LV are paced substantially simultaneously, e.g., within about 5 msec, then either chamber may be selected as the active chamber. The system is initialized 620 for automatic capture detection based on the chamber selection. The initialization process may involve, for example, activating a switch matrix to couple appropriate electrodes to an evoked response sensing channel.

Following the initialization process described in connection with FIG. 6A, the system enters automatic capture mode 630, illustrated in FIG. 6B. Chamber 2 and chamber 1 are paced 635, 640 according to the RV-LV offset. The system senses for 645 the evoked response of chamber 1. If capture is not detected 650 in chamber 1, then the system may increase 655 the pacing voltage and/or schedule 660 a backup pace.

If capture is detected 650 in chamber 1, then bradycardia therapy is confirmed. The system senses 670 for cardiac activity in the cross chamber sensing window. If cardiac activity is not detected 675 for a predetermined number of beats, then the automatic capture detection process continues 630. If cardiac activity is detected for the predetermined number of beats, then a threshold test is scheduled.

The embodiments of the present system illustrated herein are generally described as being implemented in a cardiac rhythm management system (CRMS) incorporating the functions of a cardiac defibrillator and pacemaker that may operate in numerous pacing modes known in the art. Various types of single and multiple chamber implantable cardiac defibrillators are known in the art and may be used in connection with the cardiac response classification methods of the present invention. The methods of the present invention may be implemented a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable CRMS having a microprocessor-based architecture, it will be understood that the implantable CRMS (or other device) may be implemented in any logic-based integrated circuit architecture, if desired.

Figure 7A:
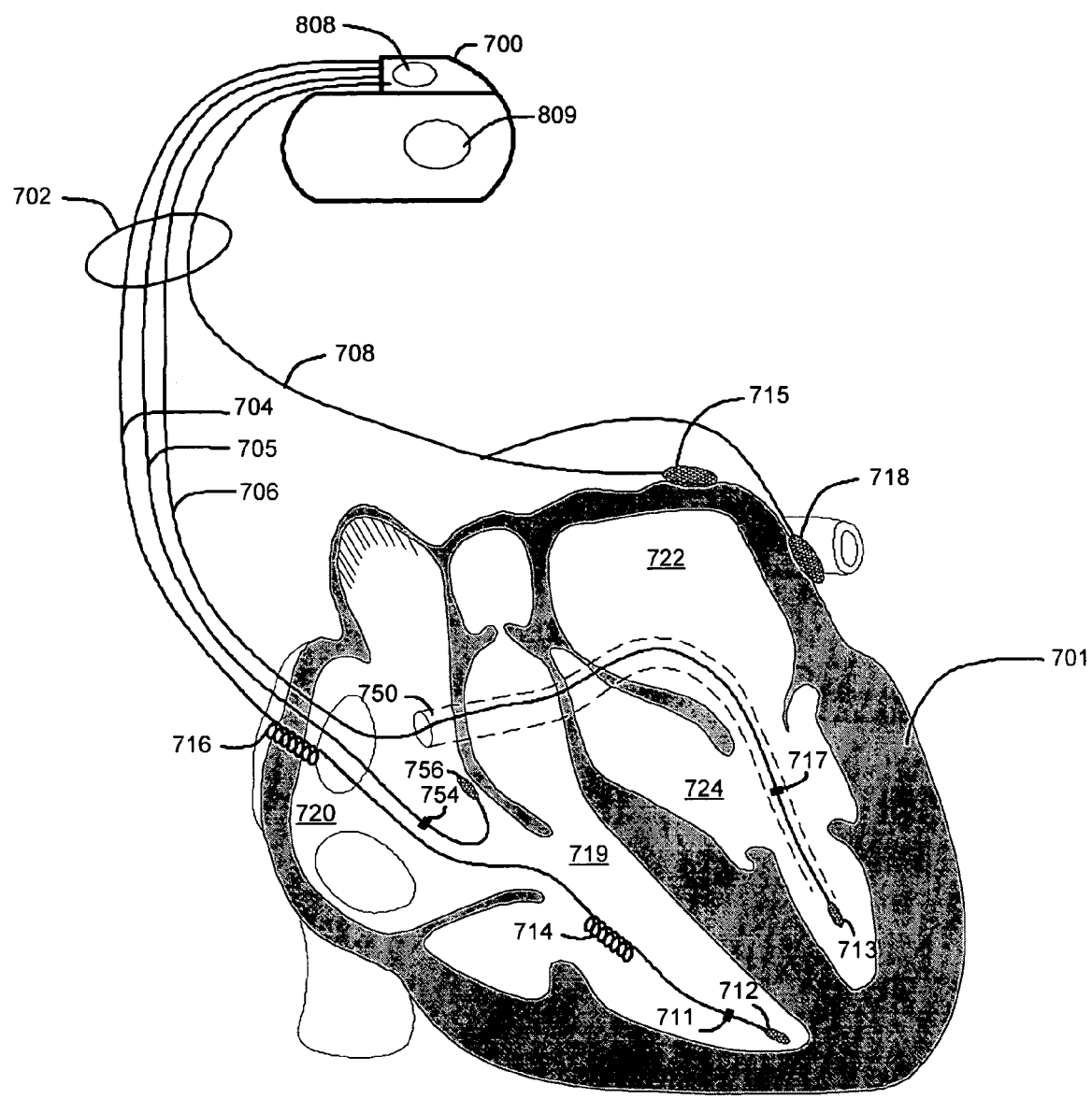
FIG. 7A illustrates a partial view of a cardiac rhythm management system that may be used to implement multi-chamber capture detection methods of in accordance with embodiments of the invention.

Referring now to FIG. 7A of the drawings, there is shown a CRMS that may be used to implement cardiac response classification methods of the present invention. The CRMS in FIG. 7A includes a pulse generator (PG) 700 electrically and physically coupled to a lead system 702. The housing and/or header of the PG 700 may incorporate one or more electrodes 808, 809 used to provide electrical stimulation energy to the heart and to sense cardiac electrical activity. The PG 700 may utilize all or a portion of the PG housing as a can electrode 809. The PG 700 may include an indifferent electrode positioned, for example, on the header or the housing of the PG 700. If the PG 700 includes both a can electrode 809 and an indifferent electrode 808, the electrodes 808, 809 typically are electrically isolated from each other.

The lead system 702 is used to detect electric cardiac signals produced by the heart 701 and to provide electrical energy to the heart 701 under certain predetermined conditions to treat cardiac arrhythmias. The lead system 702 may include one or more electrodes used for pacing, sensing, and/or defibrillation. In the embodiment shown in FIG. 7A, the lead system 702 includes an intracardiac right ventricular (RV) lead system 704, an intracardiac right atrial (RA) lead system 705, and an intracardiac left ventricular (LV) lead system 706. The CRMS illustrated in FIG. 7A is configured for biventricular pacing. The lead system 702 of FIG. 7A illustrates one embodiment that may be used in connection with the capture detection methodologies described herein. Other leads and/or electrodes may additionally or alternatively be used. For example, a CRMS may be configured for biatrial pacing. In this configuration, the CRMS may employ a left atrial lead system, such as a lead system having extracardial left atrial electrodes.

The lead system 702 may include intracardiac leads 704, 705, 706 implanted in a human body with portions of the intracardiac leads 704, 705, 706 inserted into a heart 701. The intracardiac leads 704, 705, 706 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 7A, the lead system 702 may include one or more extracardiac leads 708 having electrodes, e.g., epicardial electrodes, positioned at locations outside the heart for sensing and pacing one or more heart chambers.

The right ventricular lead system 704 illustrated in FIG. 7A includes an SVC-coil 716, an RV-coil 714, an RV-ring electrode 711, and an RV-tip electrode 712. The right ventricular lead system 704 extends through the right atrium 720 and into the right ventricle 719. In particular, the RV-tip electrode 712, RV-ring electrode 711, and RV-coil electrode 714 are positioned at appropriate locations within the right ventricle 719 for sensing and delivering electrical stimulation pulses to the heart. The SVC-coil 716 is positioned at an appropriate location within the right atrium chamber 720 of the heart 701 or a major vein leading to the right atrial chamber 720 of the heart 701.

In one configuration, the RV-tip electrode 712 referenced to the can electrode 809 may be used to implement unipolar pacing and/or sensing in the right ventricle 719. Bipolar pacing and/or sensing in the right ventricle may be implemented using the RV-tip 712 and RV-ring 711 electrodes. In yet another configuration, the RV-ring 711 electrode may optionally be omitted, and bipolar pacing and/or sensing may be accomplished using the RV-tip electrode 712 and the RV-coil 714, for example. The right ventricular lead system 704 may be configured as an integrated bipolar pace/shock lead. The RV-coil 714 and the SVC-coil 716 are defibrillation electrodes.

The left ventricular lead 706 includes an LV distal electrode 713 and an LV proximal electrode 717 located at appropriate locations in or about the left ventricle 724 for pacing and/or sensing the left ventricle 724. The left ventricular lead 706 may be guided into the right atrium 720 of the heart via the superior vena cava. From the right atrium 720, the left ventricular lead 706 may be deployed into the coronary sinus ostium, the opening of the coronary sinus 750. The lead 706 may be guided through the coronary sinus 750 to a coronary vein of the left ventricle 724. This vein is used as an access pathway for leads to reach the surfaces of the left ventricle 724 which are not directly accessible from the right side of the heart. Lead placement for the left ventricular lead 706 may be achieved via subclavian vein access and a preformed guiding catheter for insertion of the LV electrodes 713, 717 adjacent to the left ventricle.

Unipolar pacing and/or sensing in the left ventricle may be implemented, for example, using the LV distal electrode referenced to the can electrode 809. The LV distal electrode 713 and the LV proximal electrode 717 may be used together as bipolar sense and/or pace electrodes for the left ventricle. The left ventricular lead 706 and the right ventricular lead 704, in conjunction with the PG 700, may be used to provide cardiac resynchronization therapy such that the ventricles of the heart are paced substantially simultaneously, or in phased sequence, to provide enhanced cardiac pumping efficiency for patients suffering from congestive heart failure.

The right atrial lead 705 includes a RA-tip electrode 756 and an RA-ring electrode 754 positioned at appropriate locations in the right atrium 720 for sensing and pacing the right atrium 720. In one configuration, the RA-tip 756 referenced to the can electrode 809, for example, may be used to provide unipolar pacing and/or sensing in the right atrium 720. In another configuration, the RA-tip electrode 756 and the RA-ring electrode 754 may be used to effect bipolar pacing and/or sensing.

Figure 7B:
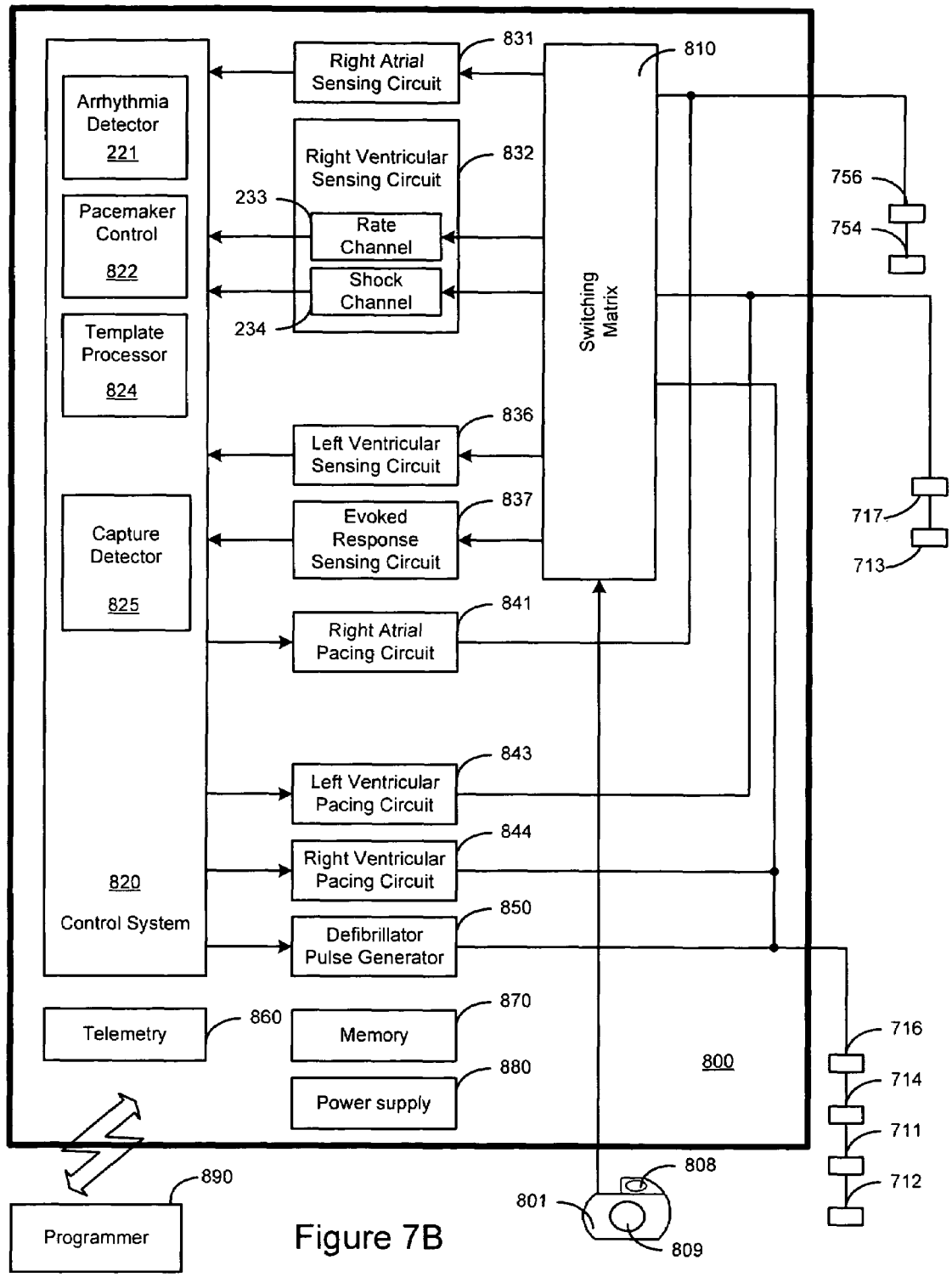
FIG. 7B is shown a block diagram of an embodiment of a cardiac rhythm management system suitable for implementing a capture detection methodology of the present invention.

Referring now to FIG. 7B, there is shown a block diagram of an embodiment of a CRMS 800 suitable for implementing a capture detection methodology of the present invention. FIG. 7B shows a CRMS divided into functional blocks. It is understood by those skilled in the art that there exist many possible configurations in which these functional blocks can be arranged. The example depicted in FIG. 7B is one possible functional arrangement. Other arrangements are also possible. For example, more, fewer or different functional blocks may be used to describe a cardiac defibrillator suitable for implementing the cardiac response classification methodology of the present invention. In addition, although the CRMS 800 depicted in FIG. 7B contemplates the use of a programmable microprocessor-based logic circuit, other circuit implementations may be utilized.

The CRMS 800 depicted in FIG. 7B includes circuitry for receiving cardiac signals from a heart and delivering electrical stimulation energy to the heart in the form of pacing pulses or defibrillation shocks. In one embodiment, the circuitry of the CRMS 800 is encased and hermetically sealed in a housing 801 suitable for implanting in a human body. Power to the CRMS 800 is supplied by an electrochemical battery 880. A connector block (not shown) is attached to the housing 801 of the CRMS 800 to allow for the physical and electrical attachment of the lead system conductors to the circuitry of the CRMS 800.

The CRMS 800 may comprise a programmable microprocessor-based system, including a control system 820 and a memory 870. The memory 870 may store parameters for capture detection along with information related to various pacing, defibrillation, and sensing modes, along with other parameters. Further, the memory 870 may store data indicative of cardiac signals received by other components of the cardiac defibrillator 800. The memory 870 may be used, for example, for storing historical EGM and therapy data. The historical data storage may include, for example, data obtained from long-term patient monitoring used for trending or other diagnostic purposes. Historical data, as well as other information, may be transmitted to an external programmer unit 890 as needed or desired.

The control system 820 and memory 870 may cooperate with other components of the CRMS 800 to control the operations of the CRMS 800. The control system depicted in FIG. 7B incorporates a capture detector 825 for detecting capture in accordance with various embodiments of the present invention. The control system 820 may include additional functional components including a pacemaker control circuit 822, an arrhythmia detector 821, and a template processor 824, along with other components for controlling the operations of the cardiac defibrillator 800.

Telemetry circuitry 860 may be implemented to provide communications between the CRMS 800 and an external programmer unit 890. In one embodiment, the telemetry circuitry 860 and the programmer unit 890 communicate using a wire loop antenna and a radio frequency telemetric link, as is known in the art, to receive and transmit signals and data between the programmer unit 890 and the telemetry circuitry 860. In this manner, programming commands and other information may be transferred to the control system 820 of the CRMS 800 from the programmer unit 890 during and after implant. In addition, stored cardiac data pertaining to capture threshold and/or capture detection, for example, along with other data, may be transferred to the programmer unit 890 from the CRMS 800.

In the embodiment of the CRMS 800 illustrated in FIG. 7B, electrodes RA-tip 756, RA-ring 754, RV-tip 712, RV-ring 711, RV-coil, SVC-coil, LV distal electrode 113, LV proximal electrode 717, indifferent electrode 808, and can electrode 809 are coupled through a switch matrix 810 to sensing circuits 831-837.

A right atrial sensing circuit 831 serves to detect and amplify electrical signals from the right atrium of the heart. Bipolar sensing in the right atrium may be implemented, for example, by sensing voltages developed between the RA-tip 756 and the RA-ring 754. Unipolar sensing may be implemented, for example, by sensing voltages developed between the RA-tip 756 and the can electrode 809. Outputs from the right atrial sensing circuit are coupled to the control system 820.

A right ventricular sensing circuit 832 serves to detect and amplify electrical signals from the right ventricle of the heart. The right ventricular sensing circuit 832 may include, for example, a right ventricular rate channel 833 and a right ventricular shock channel 834. Right ventricular cardiac signals sensed through use of the RV-tip 712 electrode are right ventricular near-field signals and are denoted RV rate channel signals. A bipolar RV rate channel signal may be sensed as a voltage developed between the RV-tip 712 and the RV-ring. Alternatively, bipolar sensing in the right ventricle may be implemented using the RV-tip electrode 712 and the RV-coil 714. Unipolar rate channel sensing in the right ventricle may be implemented, for example, by sensing voltages developed between the RV-tip 712 and the can electrode 809.

Right ventricular cardiac signals sensed through use of the RV-coil electrode 714 are far-field signals, also referred to as RV morphology or RV shock channel signals. More particularly, a right ventricular shock channel signal may be detected as a voltage developed between the RV-coil 714 and the SVC-coil 716. A right ventricular shock channel signal may also be detected as a voltage developed between the RV-coil 714 and the can electrode 809. In another configuration the can electrode 809 and the SVC-coil electrode 716 may be electrically shorted and a RV shock channel signal may be detected as the voltage developed between the RV-coil 114 and the can electrode 809/SVC-coil 716 combination.

Outputs from the right ventricular sensing circuit 832 are coupled to the control system 820. Rate channel signals and shock channel signals may be used to develop morphology templates for analyzing cardiac signals, e.g., for detecting cardiac arrhythmia. Rate channel signals and shock channel signals may be transferred from the right ventricular sensing circuit 832 to the control system 820 and to a template processor 824 where the morphological characteristics of a cardiac signal are analyzed. The template processor 824 works in combination with the control system 820 and the memory 870 to generate and maintain various types of templates, including, for example, templates used for arrhythmia discrimination as well as capture detection as described in more detail below.

A left ventricular sensing circuit 836 serves to detect and amplify electrical signals from the left ventricle of the heart. Bipolar sensing in the left ventricle may be implemented, for example, by sensing voltages developed between the LV distal electrode 713 and the LV proximal electrode 717. Unipolar sensing may be implemented, for example, by sensing voltages developed between the LV distal electrode 713 or the LV proximal electrode 717 to the can electrode 809.

Optionally, an LV coil electrode (not shown) may be inserted into the patient's cardiac vasculature, e.g., the coronary sinus, adjacent the left heart. Signals detected using combinations of the LV electrodes, 713, 717, LV coil electrode (not shown), and/or can electrodes 809 may be sensed and amplified by the left ventricular sensing circuitry 836. The output of the left ventricular sensing circuit 836 is coupled to the control system 820.

The outputs of the switching matrix 810 may be operated to couple selected combinations of electrodes 711, 712, 713, 714, 716, 717, 756, 754 to an evoked response sensing circuit 837. The evoked response sensing circuit 837 serves to sense and amplify voltages developed using various combinations of electrodes for cardiac response classification in accordance with embodiments of the invention.

The pacemaker control circuit 822, in combination with pacing circuitry for the right atrium, left ventricle, and right ventricle 841, 843, 844, may be implemented to selectively generate and deliver pacing pulses to the heart using various electrode combinations. The pacing electrode combinations may be used to effect bipolar or unipolar pacing of the heart chambers.

Bipolar or unipolar pacing pulses may be delivered to a heart chamber using various pacing vectors. The electrical signal following the delivery of the pacing pulses may be sensed through sensing electrodes coupled through the switch matrix 810 to the evoked response sensing circuit 837 and/or other sensing circuits 831, 832, 836 and used to classify the cardiac response to pacing.

For right ventricular pacing, bipolar pacing may be delivered using the RV-tip electrode 712 and the RV-ring electrode 711. Unipolar pacing may be delivered using the RV-tip 712 to can 809 vector. In an example of left ventricular pacing, bipolar pacing pulses may be delivered to the left ventricle between the LV distal electrode 713 and the LV proximal electrode 717. In another example, unipolar pacing pulses may be delivered to the left ventricle, for example, between the LV distal electrode 713 and the can 809.

In one embodiment of the invention, a switching matrix 810 is coupled to the RA-tip 756, RA-ring 754, RV-tip 712, RV-coil 714, LV distal electrode 713, LV proximal electrode 717, SVC coil 716, LA distal electrode 718, LA proximal electrode 715, indifferent, and can 809 electrodes. The switching matrix 810 may be arranged to provide connections to various configurations of pacing and defibrillation electrodes. The outputs of the switching matrix 810 are coupled to an evoked response (ER) sensing circuit 837 that serves to sense and amplify cardiac signals detected between the selected combinations of electrodes. The detected signals are coupled through the ER sensing circuit 837 to capture detection circuitry 825.

Figure 7C:
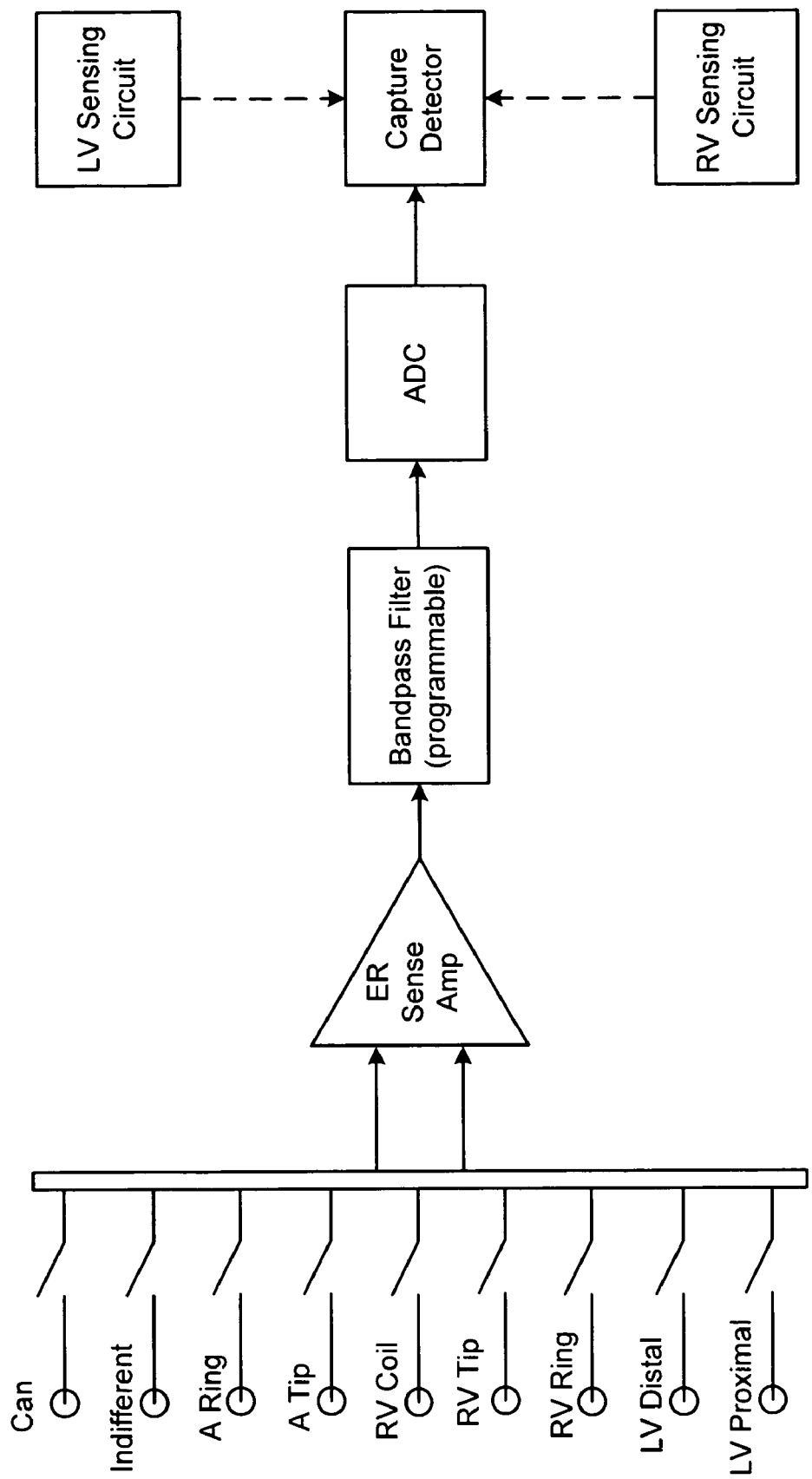
FIG. 7C depicts a block diagram illustrating an evoked response (ER) sensing channel in accordance with embodiments of the invention.

FIG. 7C depicts a block diagram illustrating an evoked response (ER) sensing channel. Electrodes pairs, selected from the can, indifferent, A-ring, A-tip, RV-coil, RV-tip, RV-ring, LV-distal, and LV-proximal electrodes, may be coupled through a switch matrix 810 to the ER sense amplifier. The switch matrix 810 allows various combinations of electrodes to be selected for capture sensing. The amplified signal is applied to a bandpass filter, which may be programmable, and digitized in an A to D converter (ADC). The digitized signal is evaluated by a capture detector to determine if a pacing pulse captured the heart chamber. In various embodiments, the capture detector may also receive inputs from other sensing circuits, including the left ventricular sensing circuit and/or the right ventricular sensing circuit, to effect the multi-chamber capture detection processes described herein.

Capture may be detected by evaluating characteristics of the sensed signal. For example, the capture detector may evaluate the peak value, rise time, peak width, slope, timing, and/or other morphological characteristics of the sensed signal to determine if the sensed signal represents an evoked response. In one embodiment, the morphology of the sensed signal may be compared to a morphology template representative of an evoked response. If the morphology of the sensed signal is consistent with the evoked response morphology template, then capture is declared.

Figure 8:
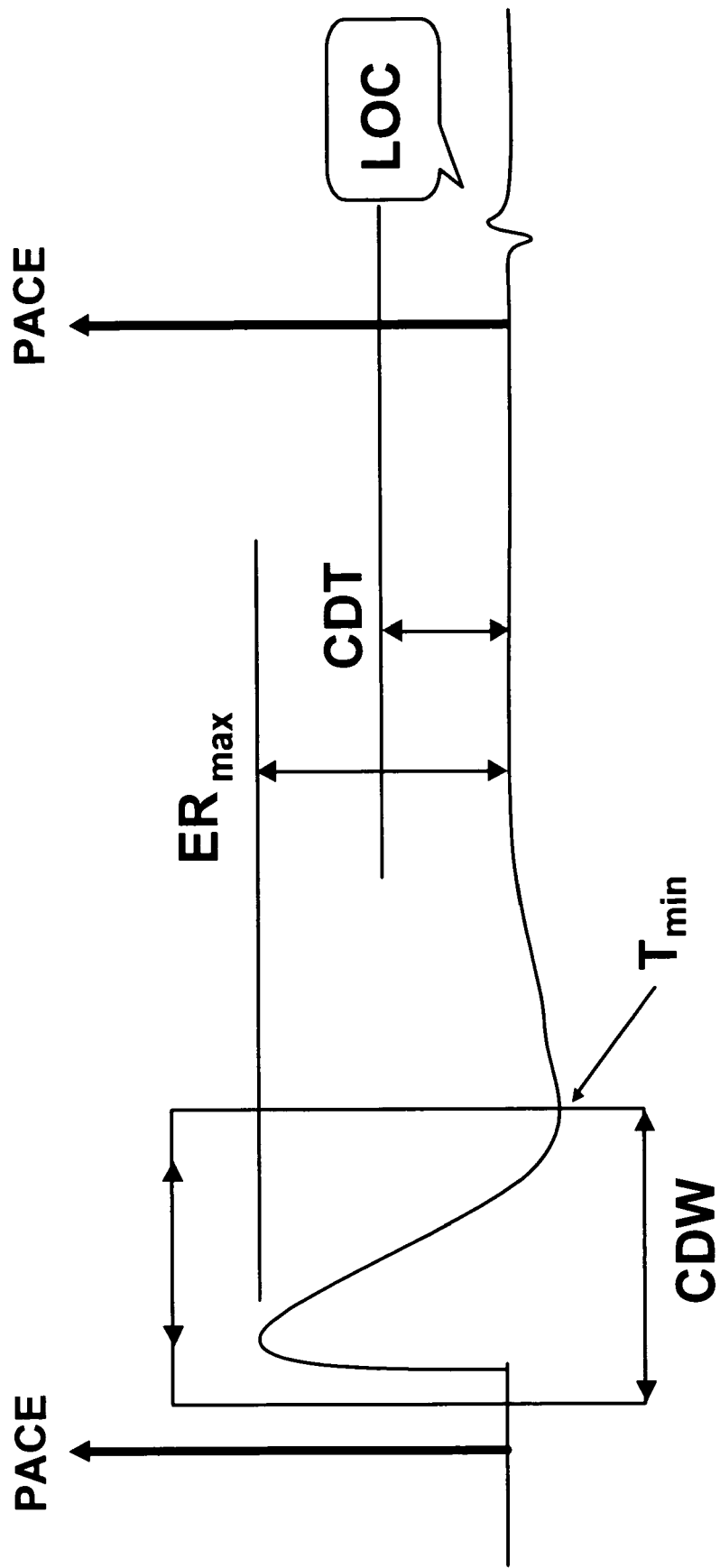
FIG. 8 is a graph illustrating signals that may be sensed by the evoked response sensing channel and used for capture detection in accordance with embodiments of the invention.

In one embodiment, illustrated by the graph of FIG. 8, the amplitude of the sensed signal is compared to a capture detection threshold (CDT). If the amplitude of the sensed signal ($ER_{max}$) meets or exceeds the capture detection threshold (CDT) within a capture detection window (CDW) following a pace, then capture is declared. For example, the capture detection window (CDW) may begin about 10 ms after the pacing pulse and continue until about 64 ms after the pacing pulse. Other values for the capture detection window may be selected based on evoked response channel characteristics, or other considerations.

For example, one implementation involves about a 15 ms to about a 55 ms capture detection window. The evoked is sensed using the same electrode that is used to pace the heart chamber, e.g., pacing is performed using V-tip and V-ring electrodes; sensing is performed using V-tip electrode and can). Such an implementation is described in commonly owned U.S. Pat. No. 6,226,551 which is incorporated herein by reference. This implementation represents one of many configurations. Other electrode configurations for sensing and pacing are possible and are included within the scope of this invention. For example, use of various electrodes for pacing and sensing in connection with detection of an evoked response is described in commonly owned U.S. Pat. No. 6,128,535 and U.S. patent application Ser. No. 10/735,519 both incorporated herein by reference. Loss capture (LOC) may be determined if the signal sensed on the evoked response channel following a pace does not meet or exceed the capture detection threshold for a predetermined number of beats. In some embodiments, LOC may be determined if evoked response channel signals following, for example, about 3 out of about 5 paces do not meet or exceed the capture detection threshold.

Figure 9:
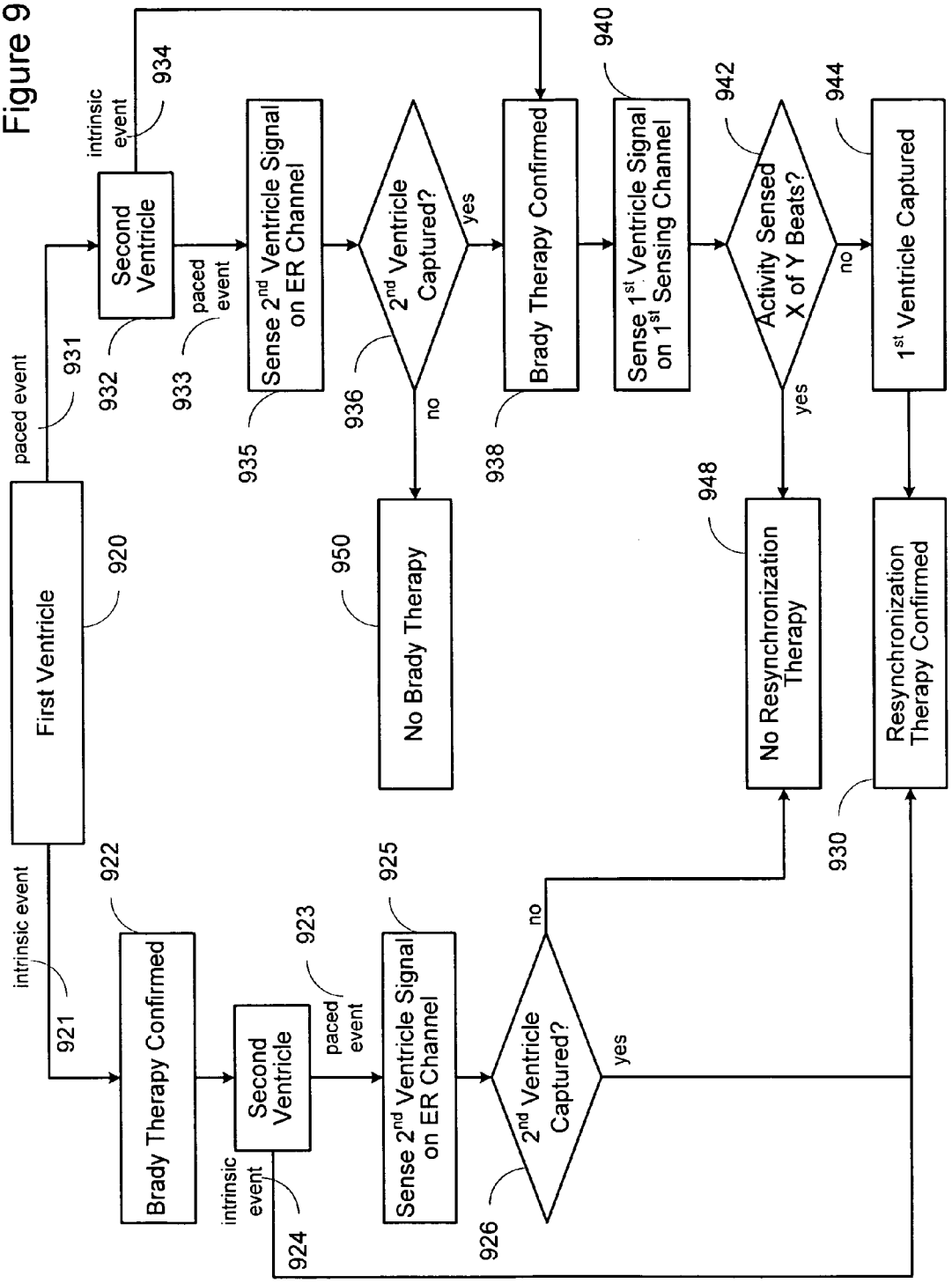
FIGS. 9-12 are flowcharts illustrating multi-chamber capture detection processes in accordance with embodiments of the invention.

The flowchart of FIG. 9 illustrates a multi-chamber capture detection process in accordance with embodiments of the invention. In this implementation, an atrioventricular delay (AVD) is initiated after an intrinsic or paced atrial event. If an intrinsic ventricular depolarization is not detected before the end of the AVD, then a first ventricle is paced. If the first ventricular event 920 is a paced event 931, then an interventricular delay (IVD), for example, a delay interval of about 0 to about 350 ms, may be initiated. A pacing pulse is delivered 933 to the second ventricle following expiration of the interventricular delay. In some embodiments, the pacing pulse delivered to the second ventricle may be inhibited if an intrinsic depolarization of the second ventricle is detected before expiration of the interventricular delay.

If an intrinsic depolarization of the second ventricle 934 is detected, then the process proceeds to check for capture of the first ventricle. If the second ventricle is paced 933, then the capture status of the second ventricle is determined based on the cardiac signal sensed 935 in the second ventricle through the ER channel. Capture may be determined by evaluating various characteristics (peak value, peak width) of the ER channel signal, or be comparing the ER channel signal to a capture template, for example. If the pacing pulse delivered to the second ventricle does not capture 936 the second ventricle, then bradycardia therapy support is not confirmed 950.

If the pacing pulse delivered to the second ventricle captures 936 the second ventricle, then bradycardia therapy is confirmed 938, and the process proceeds to determine the capture status of the first ventricle. The cardiac signal of the first ventricle is sensed 940, for example, using the sensing channel of the first ventricle, during a cross chamber sensing window that follows delivery of the second pacing pulse. If the cardiac activity sensed 942 in the first ventricle meets or exceeds a threshold value, then the first ventricle is not captured, and delivery of resynchronization therapy is not confirmed 948. If the cardiac activity sensed 942 in the first ventricle is below the threshold value, then the first ventricle is captured, and delivery of resynchronization therapy is confirmed 930.

An intrinsic depolarization of the first ventricle may be detected prior to expiration of the AVD. In this situation, the scheduled pacing pulse to the first ventricle may be inhibited. If an intrinsic depolarization of the first ventricle 921, then bradycardia therapy is confirmed 922. The second ventricle may be paced 923 to provide cardiac resynchronization therapy, or an intrinsic depolarization of the second ventricle 924 may occur. If an intrinsic depolarization of the second ventricle 924 occurs, then cardiac resynchronization therapy is confirmed 930.

If the second ventricle is paced 923, then the process determines if the second ventricular pace resulted in capture. Cardiac electrical activity in the second ventricle is sensed 925 using the evoked response channel. The cardiac activity signal is evaluated to determine the capture status of the second ventricle. For example, the cardiac activity during a capture detection window may be evaluated using any of the techniques noted above, or by other capture detection techniques. If capture of the second ventricle is detected 926, then cardiac resynchronization therapy is confirmed 930. If capture of the second ventricle is not detected 926, then cardiac resynchronization therapy is not confirmed 948.

Figure 10:
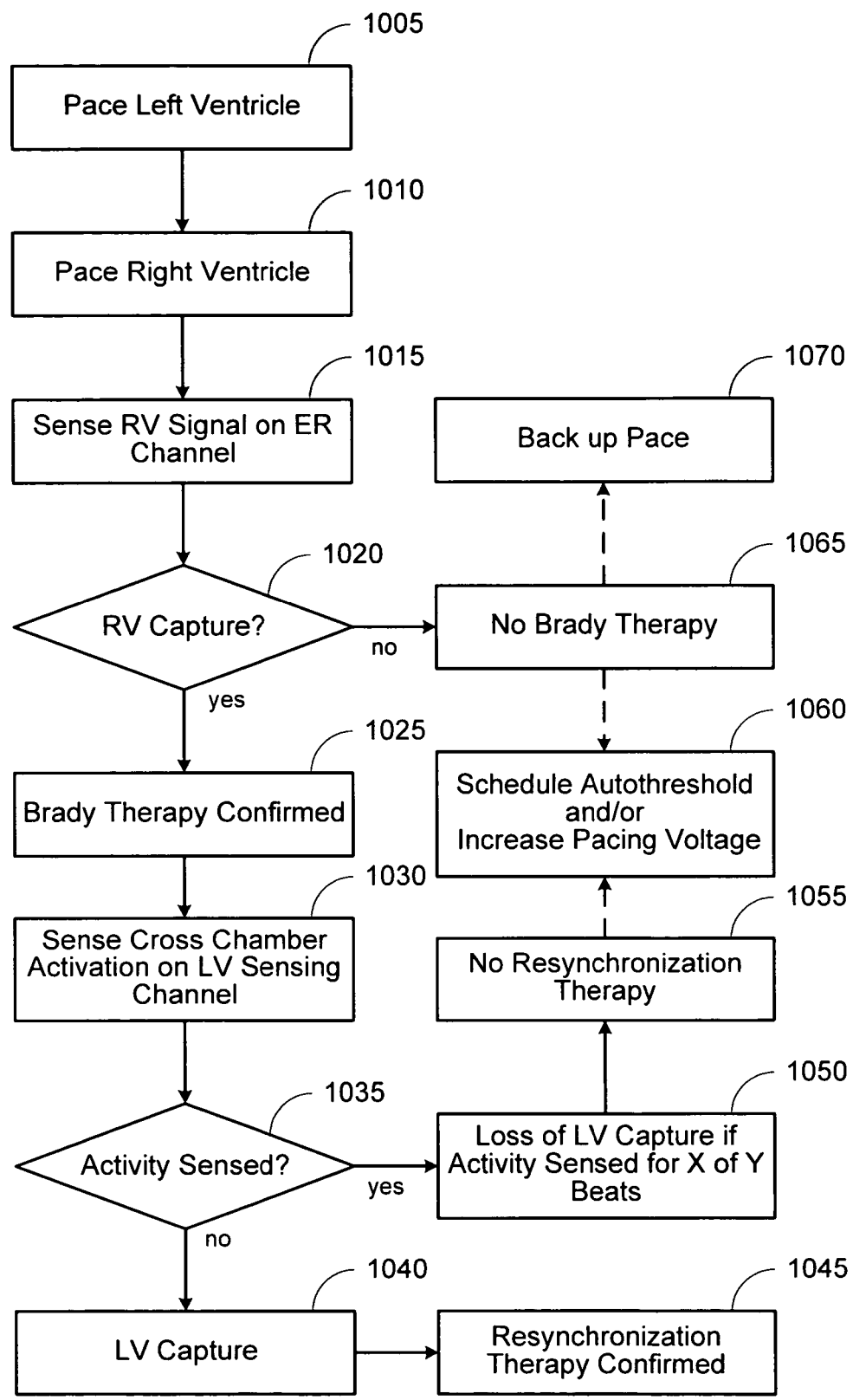
Figure 11:
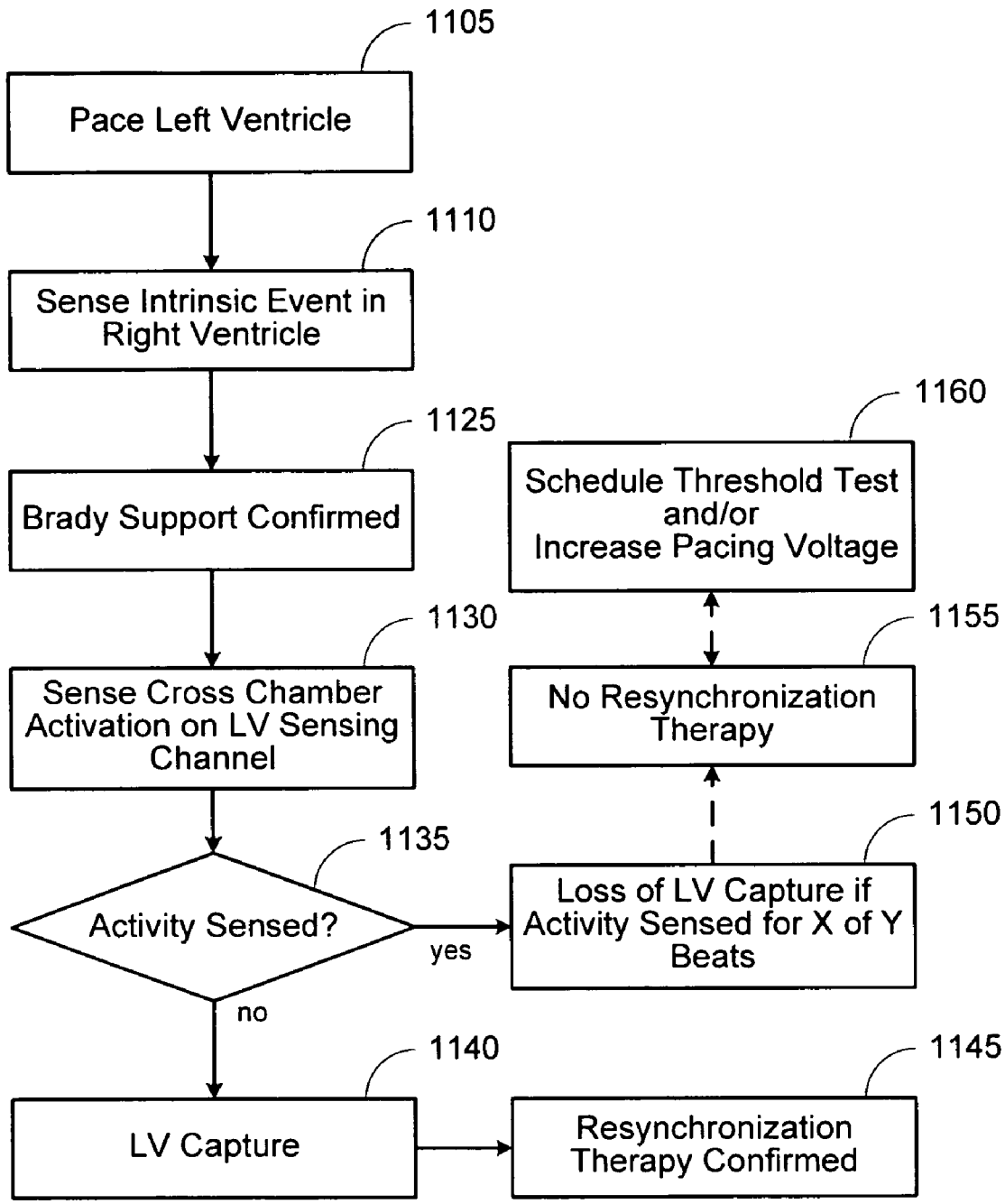
Figure 12:
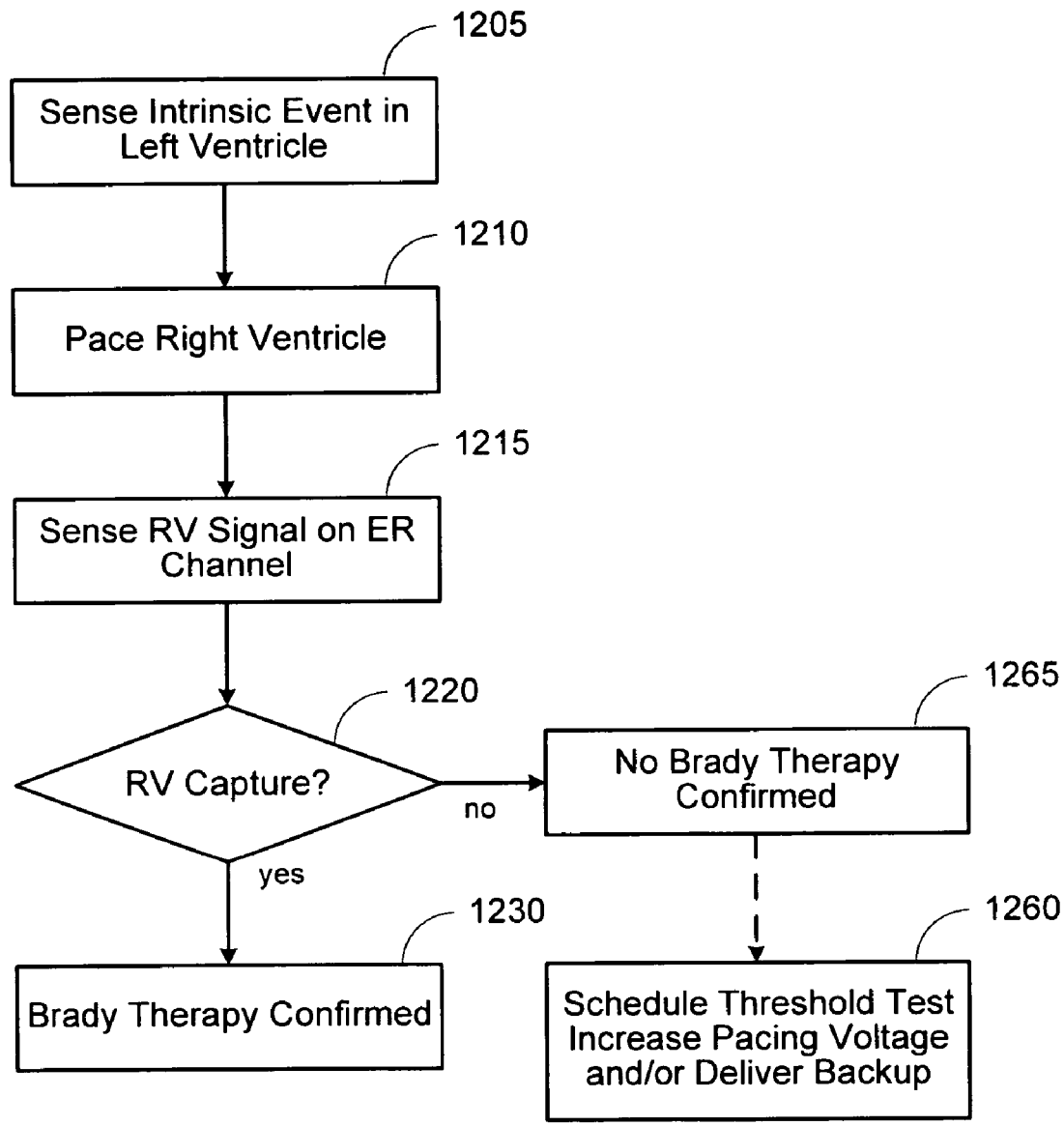

FIGS. 10-12 are flowcharts illustrating methods of multi-chamber capture detection in accordance with embodiments of the invention. The flowchart of FIG. 10 illustrates the situation wherein both left and right ventricles are paced. The flowcharts of FIGS. 11 and 12 illustrate the situations wherein one ventricle is paced and an intrinsic depolarization is detected in the other ventricle.

Turning to the flowchart of FIG. 10, the first and second ventricles are paced 1005, 1010. In this example, the first ventricle is the left ventricle and the second ventricle is the right ventricle. The opposite arrangement, e.g., the first ventricle is the right ventricle and the second ventricle is the left ventricle, could also be used. The right ventricular signal is sensed 1015 using the ER channel in a capture detection window. If right ventricular capture is not detected 1020, then bradycardia therapy is not confirmed 1065. The system may respond to a noncapture determination by scheduling 1070 a back up pace, initiating 1060 an autothreshold test, and/or increasing 1060 the right ventricular pacing voltage.

If right ventricular capture is detected 1020, then bradycardia therapy is confirmed 1025. The cross chamber activation is sensed 1030 on the LV sensing channel. Cardiac activity that meets or exceeds a threshold value 1035 in the LV indicates that the LV was not captured 1050 by the LV pacing pulse. If the left ventricle was not captured 1050, then cardiac resynchronization therapy is not confirmed 1055. The system may respond by initiating an autothreshold test and/or by increasing the left ventricular pacing voltage. Cardiac activity below the threshold value 1035 indicates that the LV pacing pulse captured 1040 the LV. Resynchronization therapy is confirmed 1045.

The flowchart of FIG. 11 illustrates the situation wherein a first ventricle is paced 1105 and an intrinsic depolarization 1110 of the second ventricle occurs. In this example, the first ventricle is the left ventricle and the second ventricle is the right ventricle. The opposite arrangement, e.g., the first ventricle is the right ventricle and the second ventricle is the left ventricle, could also be used. Detection of an intrinsic depolarization of the RV confirms 1125 bradycardia therapy support. The process proceeds to determine if the LV was captured by the LV pacing pulse. Cross chamber activation is sensed 1130 on the LV sensing channel. Cardiac electrical activity in the LV that meets or exceeds a threshold value 1135 indicates that the LV was not captured 1150 by the LV pacing pulse. If the left ventricle was not captured 1150, then cardiac resynchronization therapy is not confirmed 1155. The system may respond by initiating an autothreshold test and/or by increasing the left ventricular pacing voltage. Cardiac activity below the threshold value 1135 indicates that the LV pacing pulse captured 1140 the LV. Resynchronization therapy is confirmed 1145.

The flowchart of FIG. 12 illustrates the situation wherein an intrinsic depolarization 1205 of the first ventricle occurs and a second ventricle is paced 1210. In this example, the first ventricle is the left ventricle and the second ventricle is the right ventricle. The opposite arrangement, e.g., the first ventricle is the right ventricle and the second ventricle is the left ventricle, could also be used. Detection of an intrinsic depolarization of the LV confirms 1212 bradycardia therapy support. The process proceeds to determine if the RV was captured by the RV pacing pulse. Cardiac electrical activity in the RV is sensed 1215 on the ER channel. Capture is detected 1220 using any of the capture detection methods listed above, or other methods. If the RV was not captured 1220, then cardiac resynchronization therapy is not confirmed 1265. The system may respond by initiating 1260 an autothreshold test and/or by increasing 1260 the left ventricular pacing voltage. If the RV was captured 1220, then cardiac resynchronization therapy is confirmed 1230.

FIGS. 13A-13I are timing diagrams illustrating automatic capture detection using cross chamber sensing in accordance with embodiments of the invention. For purposes of illustration, the left ventricular event generally precedes the right ventricular event in the timing diagrams illustrated in FIGS. 13A-13I. In other scenarios, the right ventricular event could precede the left ventricular event. Selection of the sensing channels and sensing vectors used may be based on the LV-RV offset. For example, if the left ventricle is paced before the right ventricle, then the ER channel may utilize the RV-coil to Can vector to sense the electrical signal of the right ventricle. The left ventricular sensing channel may be employed to sense the cross-chamber electrical activity of the left ventricle, using, for example, the LV proximal electrode to LV distal electrode sensing vector. In the case of right ventricle paced before left ventricle, the LV-ring to Can vector may be used to sense the evoked response and the RV-tip to RV-ring may be used to sense the cross-chamber activity in the right ventricle.

Figure 13A:
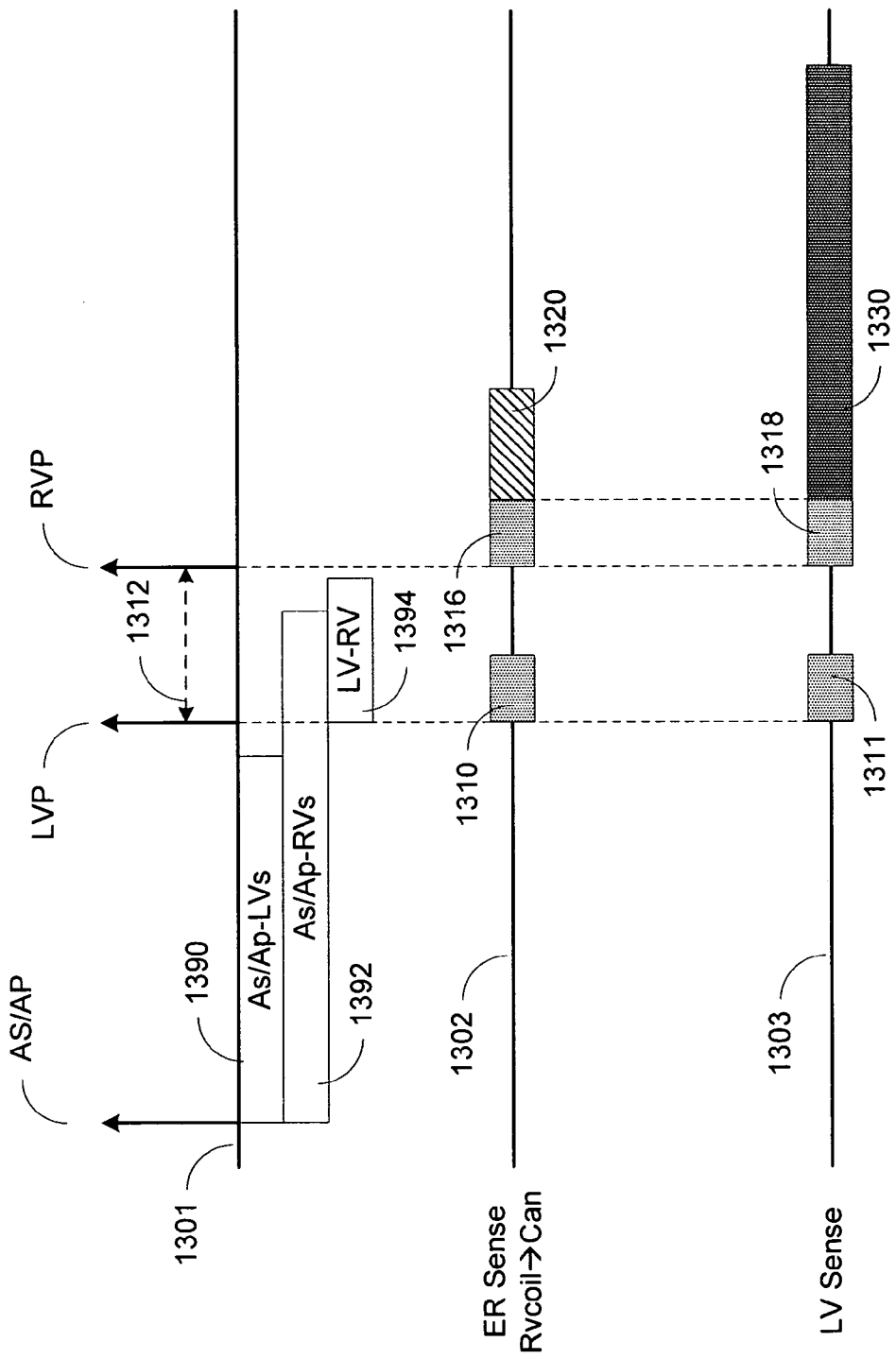
FIGS. 13A-13I are timing diagrams illustrating automatic capture detection using cross chamber sensing in accordance with embodiments of the invention.

FIG. 13A illustrates the relationships between cardiac events and various timing windows and sensing channels that may be employed for multi-chamber capture detection. The top graph 1301, illustrates the timing of cardiac events, the middle graph 1302 illustrates timing windows utilized for the ER channel, and the bottom graph 1303 illustrates timing windows utilized on the LV sensing channel. The ER channel for these illustrations is used to sense right ventricular events through the RV-coil to can sensing vector.

Following an intrinsic atrial depolarization or paced atrial event (AS/AP), a left ventricular pacing pulse (LVP) is delivered to a left ventricle. The ER channel 1305 and the LV channel 1303 are blanked 1310, 1311 following the LVP to avoid saturation of the sense channel amplifiers. In one example, the ER channel may be blanked for about 10 ms and the LV sensing channel may be blanked for about 40 ms after delivery of the LVP for a period of about 40 ms. A right ventricular pacing pulse (RVP) is delivered to the right ventricle following an interventricular delay 1312. The ER channel 1302 and the LV channel 1303 are blanked 1316, 1318 after delivery of the RVP to avoid saturation of the sense channel amplifiers. The ER channel may be blanked for about 10 ms and the LV sensing channel may be blanked for about 40 ms after the RVP.

After the ER channel blanking period 1316, a capture detection window 1320 is initiated on the ER channel 1302. The capture detection window may comprise an interval of about 10 ms to about 80 ms, for example. The system senses on the ER channel 1302 for cardiac activity during the capture detection window 1320. The cardiac signal sensed on the ER channel 1302 during the capture detection window 1320 is used to detect capture of the right ventricle.

After the LV sensing channel blanking period 1318, a cross chamber sensing interval 1330 is initiated on the LV sensing channel 1303. The cross chamber sensing window may comprise an interval of about 40 ms to about 150 ms, for example. The system senses on the LV sensing channel 1303 during the cross chamber sensing window 1330 for cardiac activity in the left ventricle responsive to the RVP. If both pacing pulses LVP, RVP captured their respective chambers, the depolarization wavefront caused by the LVP collides with a depolarization wavefront traveling in the opposite direction caused by the RVP. The collision of depolarization wavefronts cancels the cardiac signal in the left ventricle generated by the depolarization wavefront resulting from the RVP. If the left ventricle was not captured by the LVP, then no cancellation occurs, and the depolarization wavefront caused by the RVP is evident in the cardiac signal sensed on the LV sensing channel 1303 during the cross chamber sensing window 1330. Interval 1390 represents the conduction time from an atrial event (sense or pace) conducted to the left ventricle, interval 1392 represents the conduction time from an atrial event (sense or pace) conducted to the right ventricle, and interval 1394 represents the conduction time between ventricles.

Figure 13B:
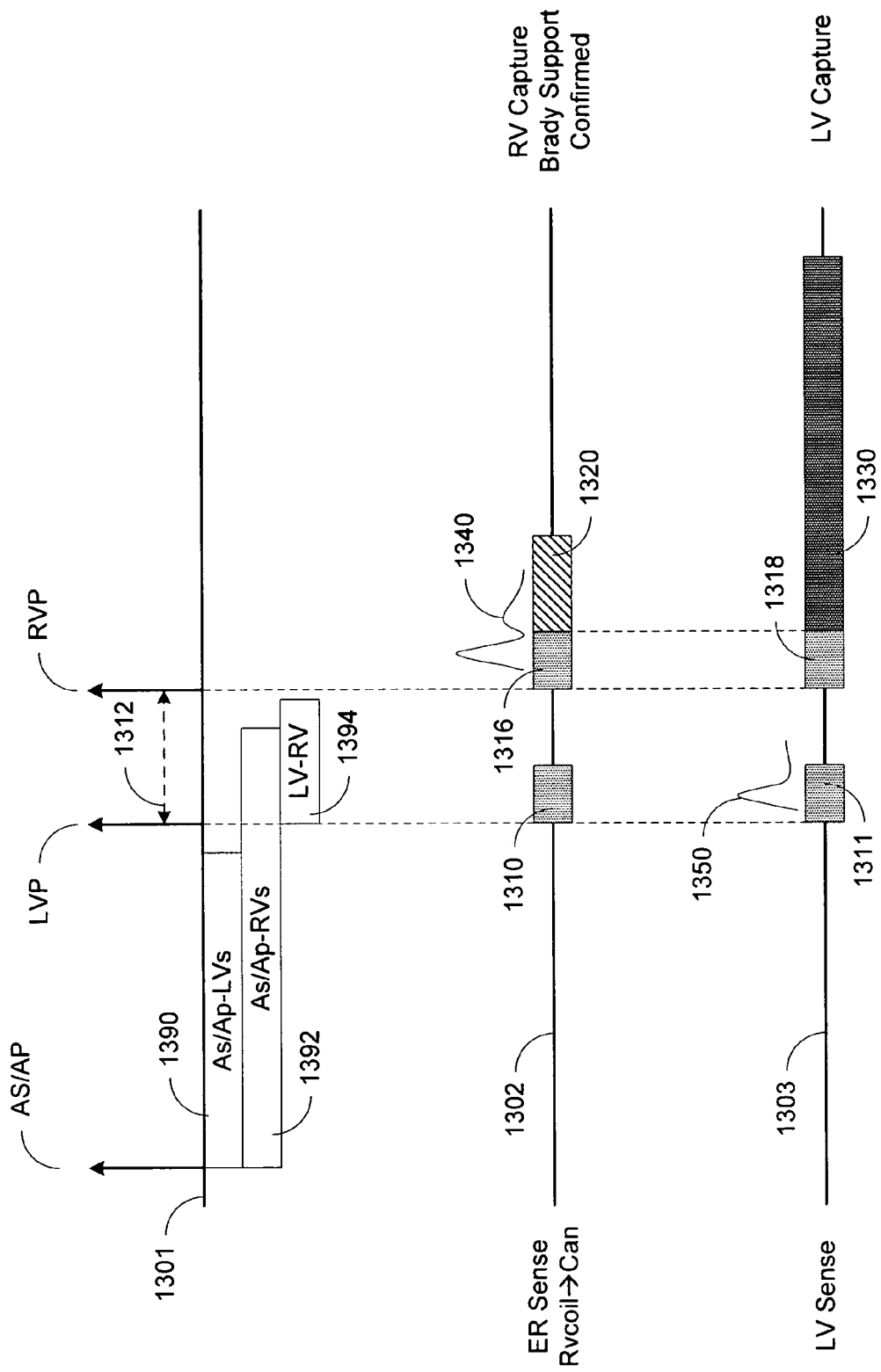

FIG. 13B is a timing diagram illustrating cardiac electrical signals sensed on the ER channel 1302 and the LV sensing channel 1303 when the LVP and the RVP produce capture of the left and right ventricles, respectively. Following the RVP, an evoked response signal 1340 detected on the ER channel 1302 during the capture detection window 1320 indicates that the RVP produced capture of the right ventricle. Detection of capture of the right ventricle confirms bradycardia support.

The electrical signal 1350 produced by the LVP is indicated during the LV sense channel blanking period 1311 following the LVP. The lack of electrical activity sensed on the LV sense channel 1303 during the cross chamber sensing window 1330 indicates the LVP captured the left ventricle.

Figure 13C:
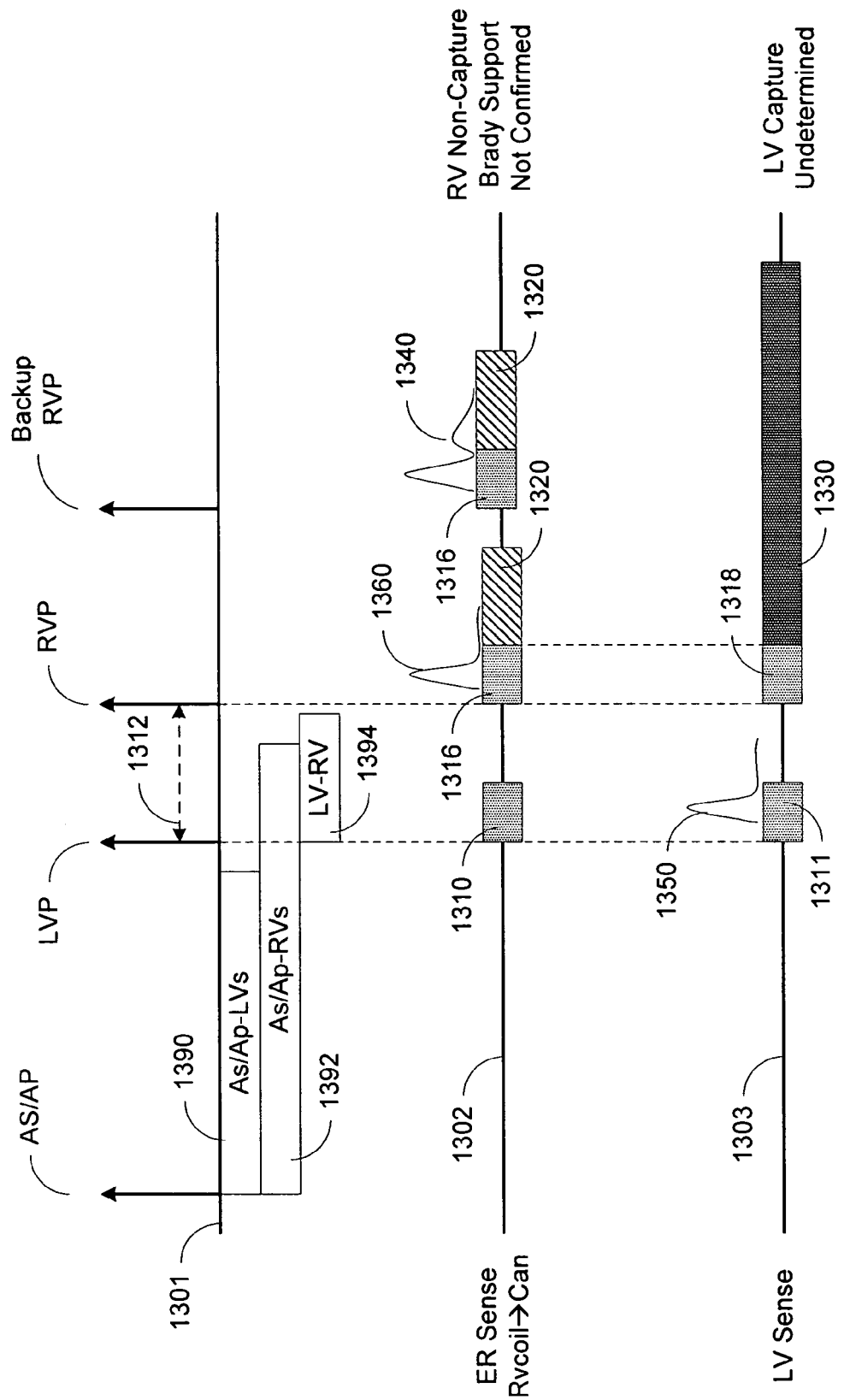

FIG. 13C is a timing diagram illustrating cardiac electrical signals indicating LVP capture and RVP noncapture. A cardiac electrical signal 1350 produced by the LVP is indicated during the blanking period 1311 of the LV sense channel 1303 following the LVP. The signal 1360 produced by the RVP is indicated during the ER channel blanking period 1310 following the RVP. The RVP does not produce capture of the right ventricle, however, as indicated by the absence of a signal above a capture detection threshold in the capture detection window 1320 of the ER channel 1302. Bradycardia therapy support is not confirmed and capture of the left ventricle by the LVP is undetermined. In this scenario, a high energy backup pace is delivered to the right ventricle. RV capture is confirmed by the evoked response 1340 sensed following the RV backup pace.

Figure 13D:
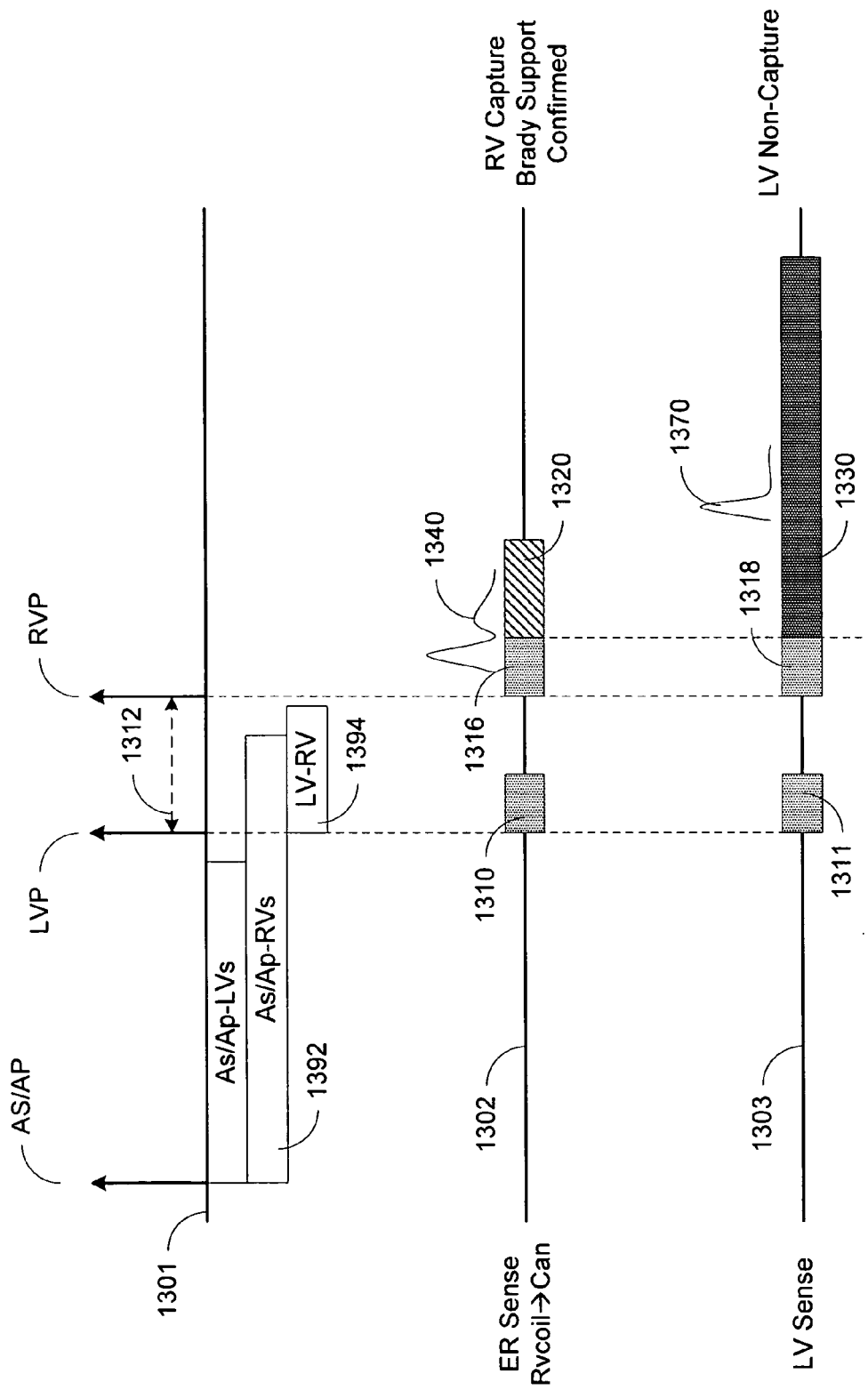

FIG. 13D is a timing diagram illustrating cardiac electrical signals representing capture of the right ventricle by the RVP and noncapture of the left ventricle by the LVP. The cardiac signal 1340 detected in the ER channel capture detection window 1320 indicates capture of the right ventricle and confirms bradycardia support. The cardiac signal detected in the cross chamber blanking window 1330 of the LV sense channel 1303 indicates noncapture of the left ventricle by the LVP.

Figure 13E:
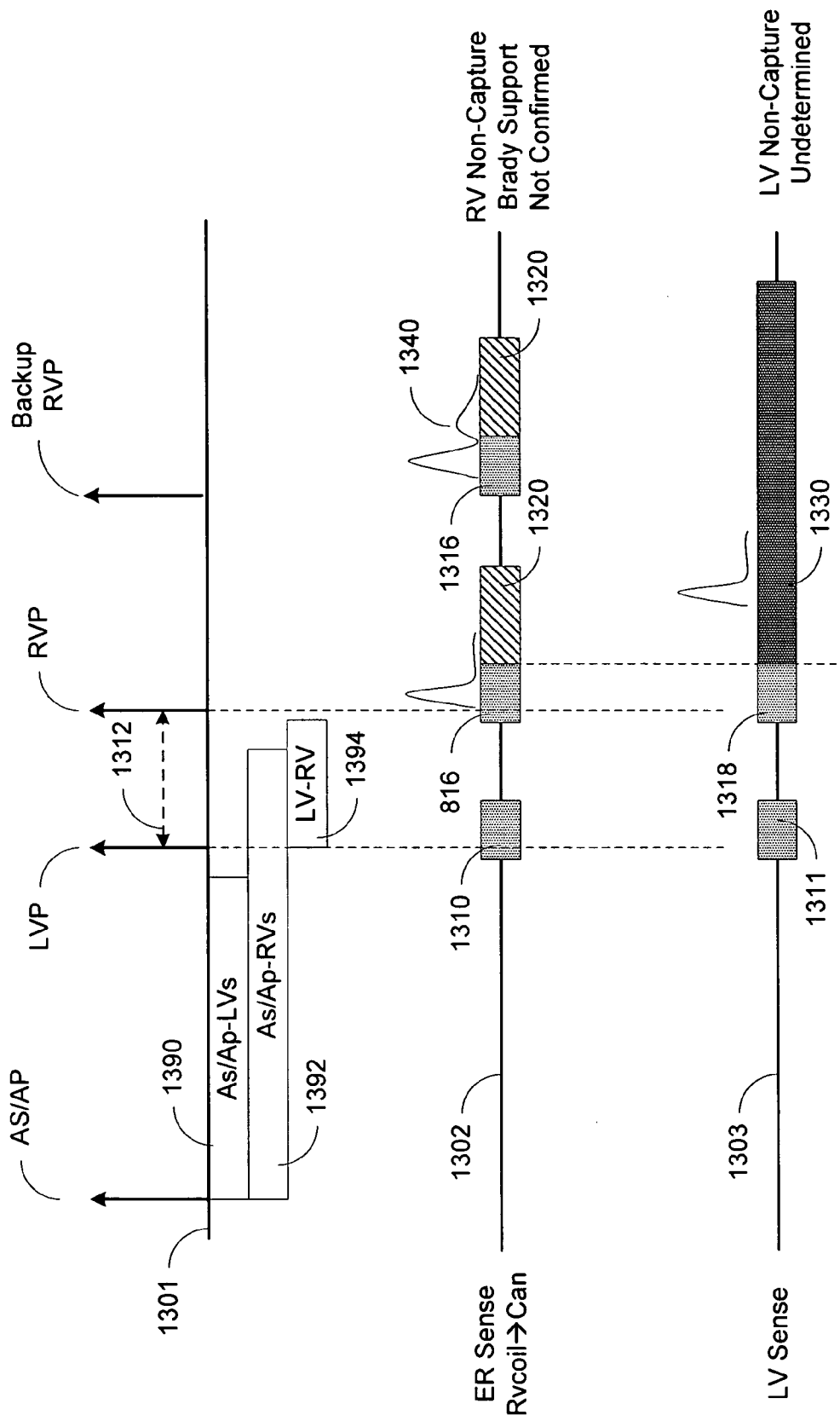

FIG. 13E is a timing diagram illustrating cardiac electrical signals representing noncapture of the right ventricle by the RVP and noncapture of the left ventricle by the LVP. The signal 1360 produced by the RVP is evident during the ER channel blanking period 1310 following the RVP. The RVP does not produce capture of the right ventricle, however, as indicated by the absence of a signal above a capture detection threshold in the capture detection window 1320 of the ER channel 1302. Bradycardia therapy support is not confirmed. The cardiac signal 1370 detected in the cross chamber sensing window 1330 of the LV sensing channel 1303 indicates noncapture of the left ventricle by the LVP. In this scenario, a high energy backup pace is delivered to the right ventricle. RV capture is confirmed by the evoked response 1340 sensed following the RV backup pace.

Figure 13F:
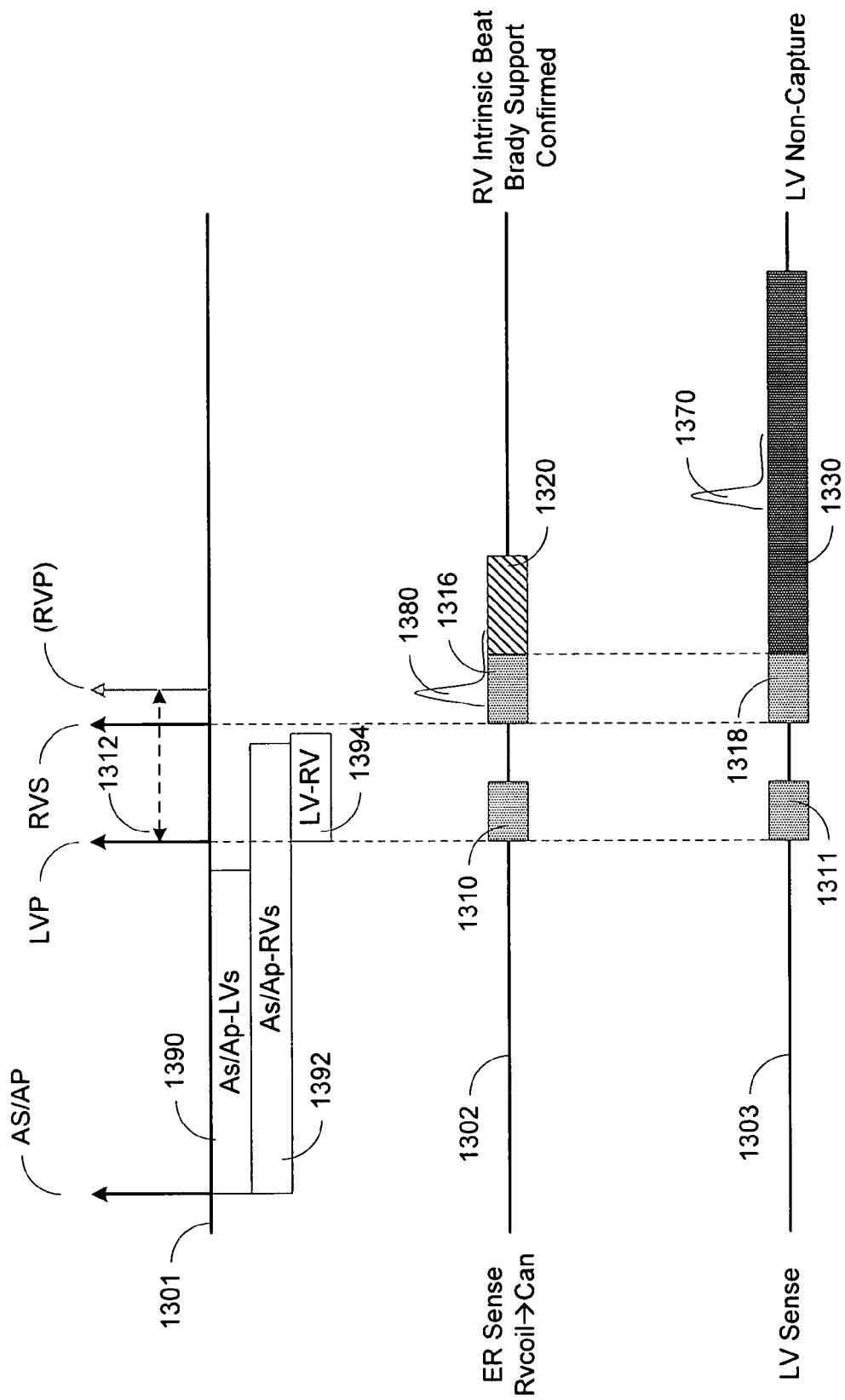
Figure 13G:
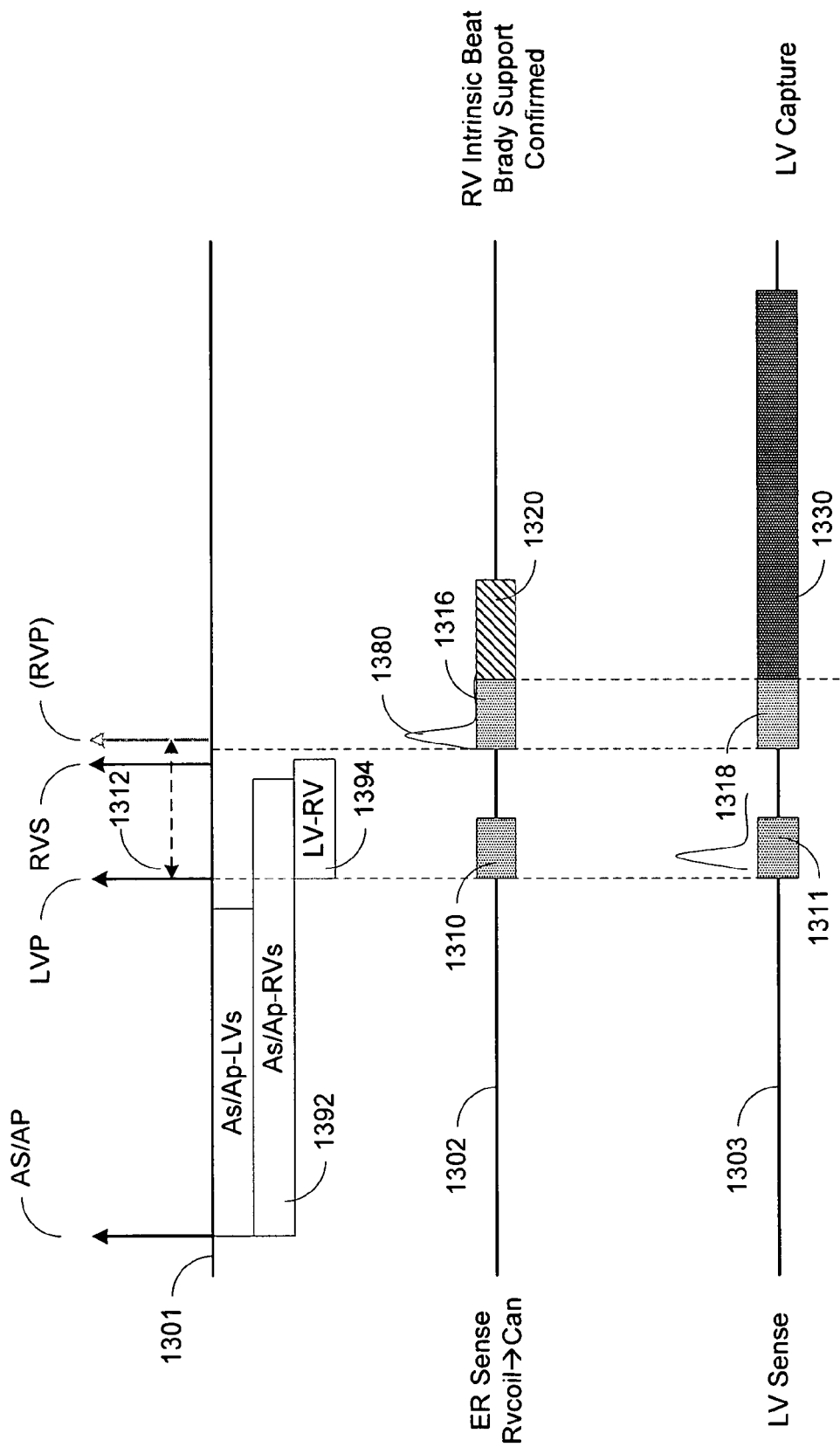

The timing diagrams of FIGS. 13F and 13G relate to cardiac electrical signals produced during a cardiac cycle that includes an intrinsic right ventricular event RVS. If an intrinsic right ventricular event RVS is sensed before delivery of a scheduled right ventricular pace, i.e., before expiration of the interventricular delay 1312, then a scheduled right ventricular pace may be inhibited. The inhibition of the right ventricular pace is indicated by parentheses enclosing the RVP. Bradycardia therapy is confirmed due to the sensed right ventricular event RVS. FIG. 13F illustrates the electrical signal 1370 indicative of left ventricular noncapture in the cross chamber sensing window 1330 of the LV sensing channel 1303. FIG. 13G illustrates the situation wherein capture of the left ventricle is accomplished. The signal in the cross chamber sensing window 1330 of the LV sensing channel 1303 is negligible, indicating left ventricular capture.

Figure 13H:
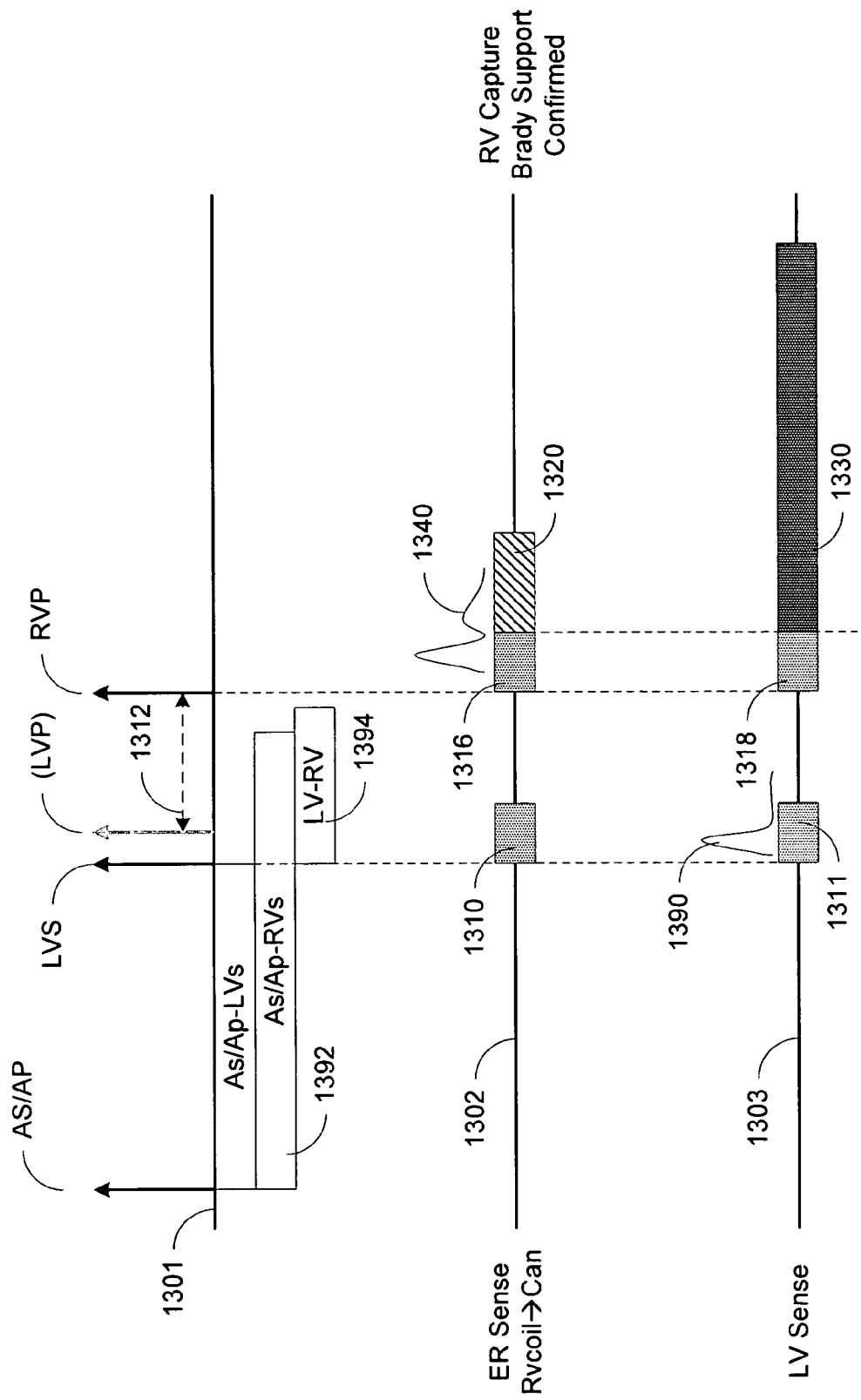
Figure 13I:
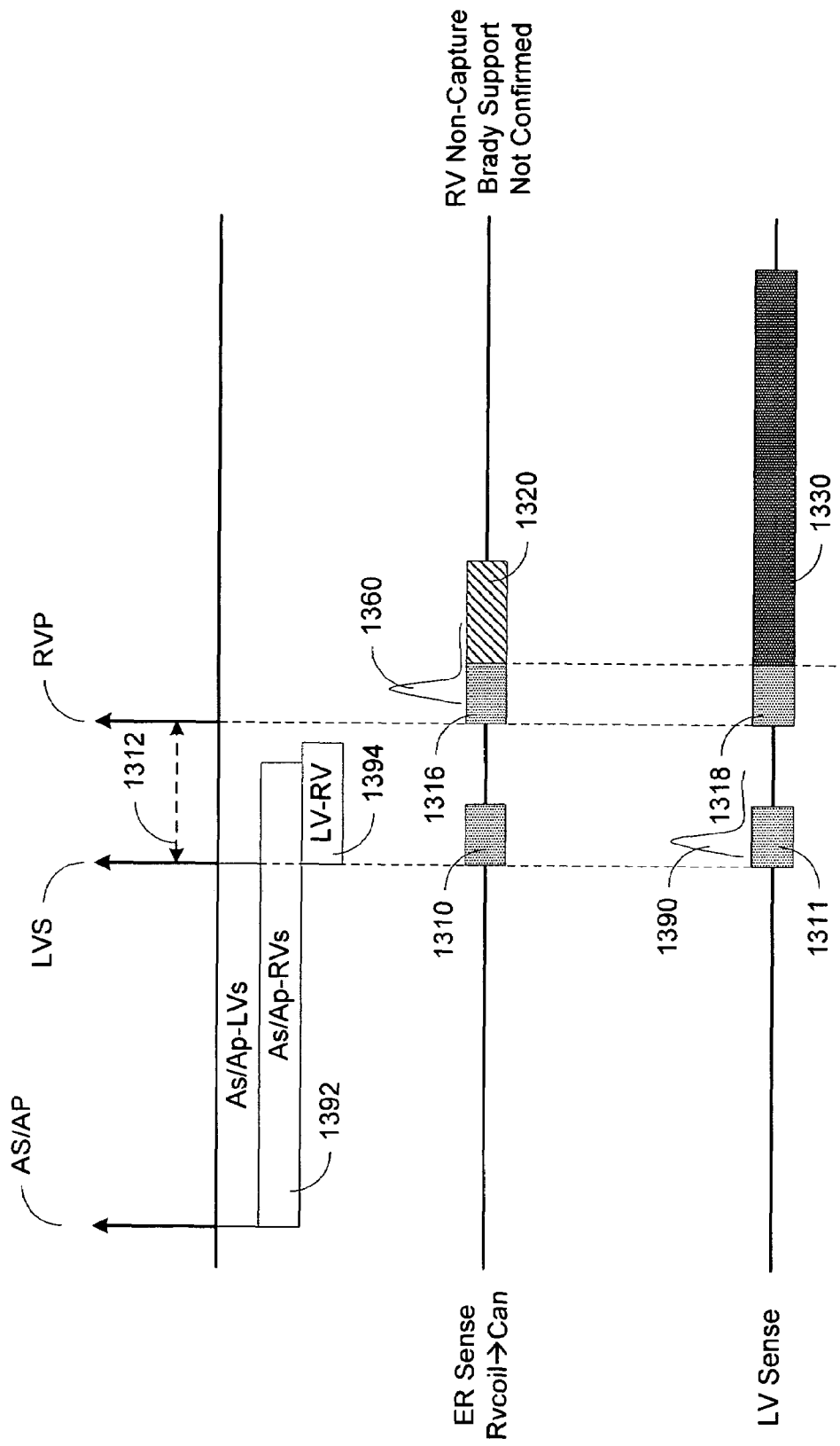

FIGS. 13H and 13I illustrate cardiac electrical signals produced during a cardiac cycle that includes an intrinsic left ventricular event LVS. An interventricular delay 1312 is initiated based on the LVS. An RVP is delivered after the interventricular delay 1312. FIG. 13H illustrated a cycle wherein right ventricular capture is detected based on the cardiac signal 1340 sensed in the ER channel blanking period 1316 of the ER channel 1302. Bradycardia therapy is confirmed. FIG. 13I illustrates a cardiac cycle wherein the RVP does not capture the right ventricle. Noncapture of the right ventricle is evidenced by a negligible signal in the ER channel blanking period 1316. Bradycardia therapy is not confirmed.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

What is claimed is:

1. A capture detection method, comprising:
   delivering a first pacing pulse to a first heart chamber;
   delivering a second pacing pulse to a second heart chamber;
   determining if the second pacing pulse captured the second heart chamber;
   sensing in the first heart chamber for a cross chamber-propagation initiated by the second pacing pulse; and
   detecting capture of the first chamber if capture of the second heart chamber is detected and if the cross-chamber propagation is not detected.

2. The method of claim 1, further comprising detecting non-capture of the first heart chamber if capture of the second heart chamber is detected and if the cross-chamber propagation is detected.

3. The method of claim 1, wherein sensing in the first heart chamber for the cross-chamber propagation comprises sensing in the first heart chamber during a cross-chamber timing interval implemented relative to the second pacing pulse.

4. The method of claim 1, wherein delivering the first pacing pulse and delivering the second pacing pulse comprises delivering the first and the second pacing pulses separated in time by a delay interval.

5. The method of claim 1, wherein delivering the first pacing pulse and delivering the second pacing pulse comprises delivering the first pacing pulse and the second pacing pulses substantially simultaneously.

6. The method of claim 1, wherein:
   delivering the first pacing pulse to the first heart chamber comprises delivering the first pacing pulse to a first ventricle; and
   delivering the second pacing pulse to the second heart chamber comprises delivering the second pacing pulse to a second ventricle.

7. The method of claim 6, further comprising performing beat by beat automatic capture detection of the second ventricle.

8. The method of claim 1, further comprising sensing in the second heart chamber for an intrinsic depolarization; wherein:
   delivering the second pacing pulse to the second heart chamber comprises delivering the second pacing pulse if a intrinsic depolarization of the second heart chamber is not sensed.

9. A cardiac rhythm management system, comprising:
   cardiac electrodes configured to electrically couple to a heart;
   a pulse generator coupled to the cardiac electrodes and configured to deliver first and second pacing pulses to first and second heart chambers respectively;
   a sensing circuit configured to sense cardiac electrical signals including cross-chamber propagation initiated by the second pacing pulse; and
   a capture detection circuit coupled to the sensing circuit and the cardiac electrodes, the capture detection circuit configured to determine if the second pacing pulse captured the second heart chamber and to detect capture of the first heart chamber if capture of the second heart chamber is detected and if the cross-chamber propagation is not detected.

10. The cardiac rhythm management system of claim 9, wherein the sensing circuit comprises:
    a first sensing channel configured to sense for the cross-chamber propagation; and
    a second sensing channel configured to sense an evoked response of the second heart chamber initiated by the second pacing pulse.

11. The cardiac rhythm management system of claim 10, wherein the first sensing channel is configured to sense for the cross-chamber propagation during a cross chamber blanking period implemented relative to the second pacing pulse.

12. The cardiac rhythm management system of claim 9, wherein the first heart chamber is a first ventricle and the second heart chamber is a second ventricle.

13. A cardiac rhythm management system, comprising:
    a pulse generator configured to deliver a first pacing pulse to a first heart chamber and a second pacing pulse to a second heart chamber;
    a capture detector configured to determine if the second pacing pulse captured the second heart chamber;
    means for sensing in the first heart chamber for a cross-chamber propagation initiated by the second pacing pulse; and
    means for detecting capture of the first chamber if capture of the second heart chamber is detected and if the cross-chamber propagation is not detected.

* * * * *

UNITED STATES PATENT AND TRADEMARK OFFICE
CERTIFICATE OF CORRECTION

| | |
|---|---|
| PATENT NO. | : 7,583,998 B2 |
| APPLICATION NO. | : 11/157426 |
| DATED | : September 1, 2009 |
| INVENTOR(S) | : Scott A. Meyer et al. |

It is certified that error appears in the above-identified patent and that said Letters Patent is hereby corrected as shown below:

<u>In the Claims</u>

Column 21, Claim 8, line 44: "a" should be --an--.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,583,998 B2  Page 1 of 1
APPLICATION NO. : 11/157426
DATED : September 1, 2009
INVENTOR(S) : Meyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this

Fourteenth Day of September, 2010

David J. Kappos
*Director of the United States Patent and Trademark Office*